(12) United States Patent
Aharinejad

(10) Patent No.: US 8,758,745 B2
(45) Date of Patent: Jun. 24, 2014

(54) USE OF GSTP1

(75) Inventor: Seyedhossein Aharinejad, Vienna (AT)

(73) Assignee: Medizinische Universitaet Wien, Vienna (AT)

( * ) Notice: Subject to any disclaimer, the term of this patent is extended or adjusted under 35 U.S.C. 154(b) by 0 days.

(21) Appl. No.: 13/505,078

(22) PCT Filed: Oct. 28, 2010

(86) PCT No.: PCT/AT2010/000408
§ 371 (c)(1),
(2), (4) Date: Apr. 30, 2012

(87) PCT Pub. No.: WO2011/050379
PCT Pub. Date: May 5, 2011

(65) Prior Publication Data
US 2012/0213761 A1 Aug. 23, 2012

(30) Foreign Application Priority Data
Oct. 30, 2009 (EP) .................................... 09174692

(51) Int. Cl.
*A61K 38/45* (2006.01)
*A61P 9/10* (2006.01)

(52) U.S. Cl.
USPC ...................................................... 424/94.5

(58) Field of Classification Search
CPC ............... G01N 2800/325; G01N 333/91177; A61K 38/45
USPC ...................................................... 424/94.5
See application file for complete search history.

(56) References Cited

U.S. PATENT DOCUMENTS

| | | | |
|---|---|---|---|
| 2006/0154261 A1* | 7/2006 | Saxon et al. | ...... 435/6 |
| 2009/0186360 A1 | 7/2009 | Mazumder et al. | |
| 2009/0215077 A1 | 8/2009 | Chandler et al. | |

FOREIGN PATENT DOCUMENTS

| EP | 1500709 A1 | 7/2003 |
|---|---|---|
| EP | 1 500 709 A1 | 1/2005 |

OTHER PUBLICATIONS

Burton, Cardiac Compromise, Apr. 14, 2007, accessed online at: jacobburton.wordpress.com /2007/04/14/cardiac-compromise/.*
Adler, Victor et al.: Regulation of JNK signaling by GSTp in: The EMBO Journal, vol. 18, No. 5, 1999, pp. 1321-1334.
Aharinejad et al.: "Abstract 4015: Abnormal Regulation of Tumor Necrosis Factor-alpha Receptor-associated Factor 2 and Downstream P38 Mitogen-activated Protein Kinase by Glutathione S-transferase P1-1 in Dilated Cardiomyopathy Patients" in Circulation, vol. 120, 2009, pp. S905.
Haberzettl et al., "Abstract 2951: Glutathione S-transferase P Deficiency Enhances Cardiovascular Sensitivity to Cyclophosphamide" in Circulation, vol. 120, 2009, pp. S718.
Luo Lan et al: "Recombinant protein glutathione S-transferases PI attenuates inflammation in mice" in: Molecular Immunology, vol. 46, No. 5, Feb. 2009, pp: 848-857.
Ohta K et al: "Association between a Variant of the Glutathione S-Transferase PI Gene (GSTP1) and Hypertension in Pregnancy in Japanese: Interaction with Parity, Age, and Genetic Factors" in: Seminars in Thrombosis and Hemostasis 200312 US LNKD-D01:10.1055/S-2004-815636, vol. 29, No. 6, Dec. 2003, pp. 653-659.
Aharinejad Seyedhossein et al: "Abnormal Regulation of Tumor Necrosis Factor-alpha Receptor-associated Factor 2 and Downstream P38 Mitogen-activated Protein Kinase by Glutathione S-transferase PI-1 in Dilated Cardiomyopathy Patients" in: Circulation, vol. 120, No. 18, Suppl. 2, Nov. 2009, p. S905.
Haberzettl Petra et al: "Glutathione S-transferase P Deficiency Enhances Cardiovascular Sensitivity to Cyclophosphamide" in: Circulation, vol. 120, No. 18, Suppl. 2, 2009-11, p. S718.
McMurray J J et al: "Heart failure", Lancet The, Lancet Limited. London, GB LNKD- DOI: 10.1016/S0140-6736(05)66621-4, vol. 365, No. 9474, May 28, 2005, pp. 1877-1889.
Abraham et al: "Selective Downregulation of VEGF-A165, VEGF-R1, and Decreased Capillary Density in Patients with Dilative but Not Ischemic Cardiomyopathy," in: Circulation Research, vol. 87, Oct. 13, 2000, pp. 644-647.
Aharinejad et al: "Differenital Role of TGF-Beta 1/bFGF and ET-1 in Graft Fibrosis in Heart Failure Patients," in: American Journal of Transplantation, vol. 5, 2005, pp. 2185-2192.
Aharinejad et al.: "Colony-Simulation Factor-1 Transfection of Myoblasts Improves the Repare of Failing Myocardium Following Autologous Myoblast Transplantation," in Cardiovascular Research, vol. 79, 2008, pp. 395-404.
Costello-Boerrigter et al: "Amino-Terminal Pro-B-Type Natriuretic Peptide and B-Type Natriuretic Peptide in the General Community Determinants and Detection of Left Ventricular Dysfunction," in J Am Coll Cardiol., vol. 47 No. 2, Jan. 17, 2006, pp. 345-353.
Lee et al., "Relation of Disease Pathogenesis and Risk Factors to Heart Failure with Preserved or Reduced Ejection Fraction: Insights From the Framingham Heart Study of the Nation Heart, Lung and Blood Institute," in Ciruclation, vol. 119, 2009, pp. 3070-3077.
Melen et al, "Interactions Between Glutathione S-Transferase P1, Tumor Necrosis Factor, and Traffic-Related Air.Pollution for Development of Childhood Allergic Disease," in Environmental Health Perspectives, vol. 116, No. 8, Aug. 2008, pp. 1077-1084.
Praffl et al, "A New Mathematical Model for Relative Quantification in Real-Time RT-PCR," in Nucleic Acids Research, vol. 29, No. 9, 2001, pp: 2002-2007.
Schaefer et al, "Impaired VE-Cadherin/Beta-Catenin Expression Mediates Endothelial Cell Degernation in Dilated Cardiomyopathy," in Circulation, vol. 108, 2003, pp: 1585-1591.
Wu et al, "Human Glutathione S-Transferase P1-1 Interacts with TRAF2 and Regulates TRAF2-ASK1 Signals," in Oncogene, vol. 25, 2006, pp. 5787-5800.

* cited by examiner

Primary Examiner — Karen Cochrane Carlson
Assistant Examiner — Jennifer M. H. Tichy
(74) Attorney, Agent, or Firm — Joyce von Natzmer; Agris & von Natzmer LLP

(57) ABSTRACT

The invention discloses the use of glutathione S-transferase P1 (GSTP1) for the prevention or treatment of cardiomyopathies or ischemic heart diseases and for the diagnosis thereof.

16 Claims, 12 Drawing Sheets

USE OF GSTP1

Figure 1:
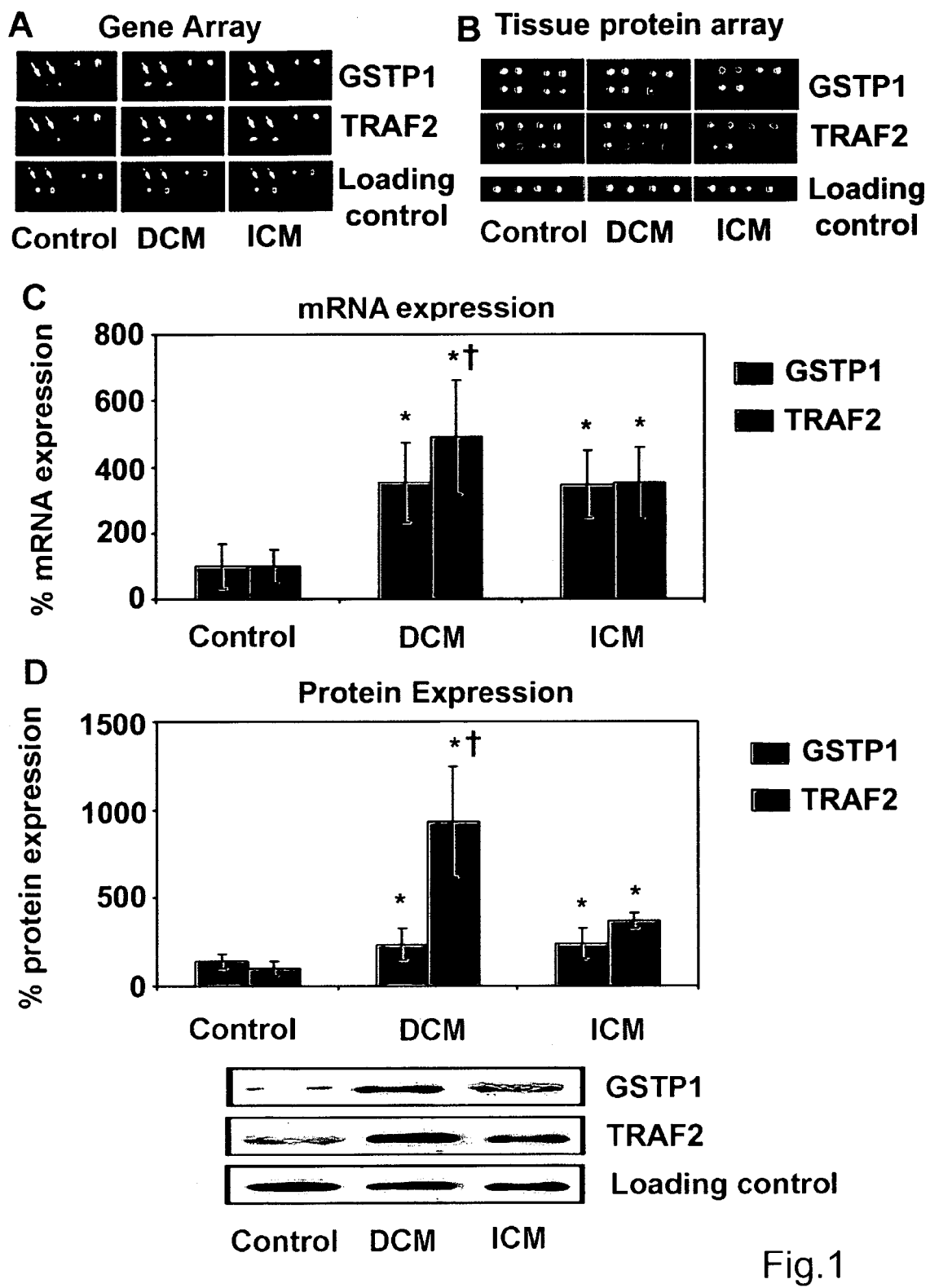

This is the U.S. national stage of International application PCT/AT2010/000408, filed Oct. 28, 2010 designating the United States and claims priority to European application no. EP 09174692.5, filed Oct. 30, 2009.

The present invention relates to the use of Glutathione-S-transferase P1.

The glutathione S-transferases (GSTs) are a multigene family of isozymes that catalyze the nucleophilic attack of the sulfur atom of glutathione (GSH) on electrophilic groups of substrate molecules. GSTs are known as detoxicating enzymes which conjugate toxic substances with GSH to become more water-soluble products which can be metabolised in the liver and finally excreted out of the body. On the basis of the amino acid sequence, the mammalian GSTs are divided into six classes: alpha, mu, omega, pi, theta and zeta. Among these isozymes, glutathione S-transferase P1 (GSTP1; GST-pi, GSTP1-1) is the most prevalent one in mammalian cells. GSTP1 has also generated interest as a neoplastic marker because it is overexpressed in a variety of different human malignancies, including lung, colon, stomach, esophagus, mouth, kidney, ovary and testicular cancers. Most prostate cancer types contain decreased levels of GSTP1 polypeptide relative to normal prostate tissue due to hypermethylation of the GSTP1 promoter resulting in decreased transcription of GSTP1 (US 2009/0186360 A1). GSTP1 is determinant in cellular response to oxidative stress and protects tumor cells from apoptosis elicited by a variety of cytotoxic agents, such as $H_2O_2$, UV, cisplatin, adriamycin, etoposide, thiotepa, chlorambucil, ethacrynic acid and arsenic trioxide. GSTP1 is therefore considered as a promising target in tumour medicine, both as a target for drug action and as a tumor marker.

GSTP1 also participates in the regulation of stress signalling and protects cells against apoptosis by the mechanisms related to its non-catalytic and ligand-binding activities. For example, GSTP1 prevents LPS-induced excessive production of proinflammatory factors and plays an anti-inflammatory role in response to LPS. GSTP1 expression, both at transcriptional and translational levels, is up-regulated by LPS stimulation. GSTP1 also functions as an endogenous inhibitor of JNK (c-Jun $NH_2$-terminal kinase), via interaction with the C-terminus. It could also be demonstrated that exogenous (recombinant) GSTP1 protein could be delivered into macrophages and suppressed iNOS and COX-2 expression in cells. Furthermore, intraperitoneally administered GSTP1 protein to mice decreased mortality of endotoxic shock significantly and inhibited acute lung injury and peritonitis (Luo et al., Mol. Immunol. 46 (2009), 848-857).

EP 1 500 709 A1 suggests GSTP1 as one of 22 inflammation markers.

Various isoforms of GSTP1 have also been found relevant to asthma and childhood allergic diseases due to the interaction of GSTP1 with air pollution from traffic (and tobacco smoke) in the respiratory system, as well as association with hypertension in pregnancy (Ohta et al., Sem. Thr. Hem. 29 (2003), 653-659).

Cardiomyopathies (CMP) are a heterogeneous group of diseases, including the dilative (DCM), the most frequent entity among cardiomyopathies, and ischemic (ICM) forms. Although pharmacotherapy and surgical interventions have been improved with survival benefit in CMP, causal treatment remains to be a vague goal. Therefore, identification of unknown mechanisms that mediate CMP could be beneficial. Results of the last decade's work clearly provide evidence that inflammation and enhanced release of pro-inflammatory cytokines, especially tumor necrosis factor (TNF)-α might play a role in the pathogenesis of CMP. However, clinical trials have paradoxically indicated a more complicated role for TNF-α in CMP that casted doubts whether TNF-α is a viable therapeutic target for CMP. The pathology of IHD is immediately related to the development of CMP, patients currently receive medications such as beta-blockers or angiotensin converting enzyme (ACE)-blockers with the goal to ameliorate the patient's symptoms and to prevent or delay the development of (ischemic) CMP due to IHD. It is therefore common to use therapies for CMP also for IHD. Importantly, patients who develop CMP based on IHD, in particular end-stage CMP, have currently only limited therapeutic options (e.g. cardiac transplantation or the use of ventricular assist devices, which can be in turn offered only to a limited number of patients).

There is still an unmet need for further drug targets and treatment regimen for efficiently preventing and treating CMP and IHD and one of its major causes, that is ischemic heart diseases (also called coronary heart diseases that can result in myocardial infarction), especially elevated blood pressure-induced CMP and volume-induced CMP.

Cardiomyopathies result in recurrent exacerbation leading to hospitalization or death. Therefore, also close surveillance and thorough clinical tests are required to achieve the optimal tailored cardiomyopathy treatment in these patients, associated with tremendous health care costs. A biomarker that could identify the evolution of cardiomyopathy and help to optimize treatment monitoring and outcome is therefore highly desirable. Ideally, such a test should be sensitive, specific, none-invasive, quick and cheap. Although, a number of neurohumoral factors and inflammatory cytokines have been reported as diagnostic biomarkers in cardiomyopathy, brain-type natriuretic peptide (BNP) and its inactive N-terminal fragment (proBNP) have gained the broadest acceptance in clinical diagnosis and monitoring of patients with suspected or established chronic CMP. However, circulating BNP and proBNP levels are dramatically affected by renal function and are age- and gender-dependent. In addition, it remains unknown whether proBNP could be beneficial in diagnosis of preserved as opposed to reduced ejection fraction (EF) CMP.

It is therefore also an object of the present invention to provide diagnostic means for cardiomyopathies and ischemic heart diseases.

Therefore, the invention provides Glutathione S-transferase P1 (GSTP1) for the prevention or treatment of cardiomyopathies (CMPs) as well as for the prevention or treatment of ischemic heart diseases. With the present invention it could be surprisingly shown that GSTP1 is beneficial in CMP treatment and in the treatment of ischemic heart diseases (IHD). GSTP1 has been described as a relevant protein in cancer medicine (e.g. U.S. Pat. No. 5,427,917 A, U.S. Pat. No. 5,552,277 A and WO 98/21359 A1) and in allergic diseases, such as asthma, especially in connection with traffic-related air pollution (e.g. Melen et al., Env. Health Persp. 116 (2008), 1077-1084). GSTP1 has also been suggested to decrease mortality of endotoxic shock and inhibition of acute lung injury and peritonitis (Luo et al., Mol. Immunol. 46 (2009), 848-875). GSTP1 was reported to interact with TRAF2 (tumor necrosis factor receptor-associated factor 2) as a novel ligand-binding function of GSTP1 in regulating kinase signalling (Wu et al., Oncogene 25 (2006), 5787-5800). Although this provided a new insight for analysing the mechanism utilized by GSTP1 to protect cells against different injury stimuli such as cytokines, UV or $H_2O_2$, and this teaching was regarded as conceivable that GSTP1 functions as a general survival factor by forming GSTP1-TRAF2 complex in tumor cells, inhibition of this complex was regarded as being limited to antitumor therapy.

According to the present invention it was surprisingly found that GSTP1 is specifically upregulated in CMP and IHD patients as compared to controls. It was further found that recombinant GSTP1 mediated GSTP1-TRAF2 association, decreased pro-inflammatory JNK1 and p38 activation and TRAF2 expression dependent on its dose and the underlying form of CMP. This enabled the provision of a new therapy strategy for CMP and IHD by administration of GSTP1. Since GSTP1 ameliorates TNF-α-mediated activation of pro-inflammatory JNK1/p38 by association to TRAF2, GSTP1 is not only beneficial in CMP and IHD treatment but also for the prevention of CMP and IHD, especially in risk patients, such as hypertensive patients.

The present invention provides the use of GSTP1 for the manufacture of a medicament for the prevention or treatment of CMP and ischemic heart diseases. The treatment of CMP and IHD according to the present invention involves the administration of an effective amount of GSTP1 to an individual in need of such treatment, e.g. human CMP and IHD patients. For these reasons and based on the fact that the pathology of IHD is immediately related to the development of CMP, patients currently receive medications such as beta-blockers or angiotensin converting enzyme (ACE)-blockers with the goal to ameliorate the patient's symptoms and to prevent or delay the development of (ischemic) CMP due to IHD. The close relationship of the pathology of IHD with CMP that is based on the remodelling of myocardium in patients with IHD, specially in patients developing myocardial infarction due to IHD that in turn leads to remodelling of the cardiac chambers and subsequently to impaired pump function of the heart, a pathological condition that is common to CMP and IHD, specially in myocardial infarction patients, shows the effectiveness of the present invention for the prevention or treatment of IHD and CMP. Therefore, it is evident that the present invention is also suitable for prevention or treatment of IHD. Importantly, patients who develop CMP based on IHD, in particular end-stage CMP, have currently only limited therapeutic options (e.g. cardiac transplantation or the use of ventricular assist devices, which can be in turn offered only to a limited number of patients) and this fact constitutes a preferred use of the present invention in order to prevent or treat patients suffering from IHD, aimed to prevent the development of CMP at the one hand and to improve or stabilise the clinical condition in IHD patients on the other.

With the present invention all forms and stages of CMP and IHD, acute and chronic forms thereof, can be treated, independently of the genesis of the CMP or IHD. Of course, the term "treatment" includes preferentially the amelioration of the disease and the prevention or slowing of progression of the disease. For example, CMPs can be caused by myocardial infarction, can be idiopathic dilative or be caused by hypertension. All these forms can be treated with GSTP1 according to the present invention. Specifically ischemic CMPs e.g. caused by myocardial infarction can be treated with GSTP1, however, also non-ischemic forms can be treated (e.g. idiopathic dilated CMPs or hypertension- or volume-induced CMPs). Since in all these CMPs, inflammatory pathways are involved, this makes them eligible for treatment with GSTP1 according to the present invention (even rare forms of CMP, if such inflammatory pathways are involved).

Therefore, preferred CMPs according to the present invention are dilated cardiomyopathy, especially congestive cardiomyopathy; obstructive hypertrophic cardiomyopathy, especially hypertrophic subaortic stenosis; other hypertrophic cardiomyopathies, especially nonobstructive hypertrophic cardiomyopathy; endomyocardial (eosinophilic) disease, especially endomyocardial (tropical) fibrosis or Löffler's endocarditis; endocardial fibroelastosis, especially congenital cardiomyopathy; other restrictive cardiomyopathies, especially constrictive cardiomyopathy NOS (not otherwise specified (according to ICD-10)); alcoholic cardiomyopathy, cardiomyopathies due to drugs and other external agents, unspecified cardiomyopathies, especially cardiomyopathy (primary)(secondary) NOS; cardiomyopathy in infectious and parasitic diseases, especially cardiomyopathy in diphtheria; cardiomyopathy in metabolic diseases, especially cardiac amyloidosis; cardiomyopathy in nutritional diseases, especially nutritional cardiomyopathy NOS; Gouty tophi of heart or thyrotoxic heart disease.

Specifically preferred forms of CMP or IHD to be treated (or prevented) according to the present invention are CMPs caused by ischemia, especially by myocardial infarction; by hypertension, or by myocarditis. GSTP1 treatment according to the present invention is therefore preferably applied in patients with acute myocarditis, preferably infective myocarditis, especially septic myocarditis; isolated myocarditis, myocarditis in a bacterial disease, especially diphtheritic, gonococcal, meningococcal, syphilitic or tuberculous myocarditis; myocarditis in a viral disease, especially influenzal myocarditis or mumps myocarditis; acute or chronic myocarditis in Chagas' disease, myocarditis in toxoplasmosis, rheumatoid myocarditis or sarcoid myocarditis.

The preferred indications according to the present invention are therefore those listed under Chapter IX of the ICD-10 (I11-I15, especially I21, I22 and I23; I20-I25, especially I21 and I22; I40-I43, especially I42; I50-I57, especially I50 and I57).

The main focus of the present invention is the treatment of human patients; however, based on the present findings, it is clear that also animal (mammal) CMP and IHD in which inflammation is involved can be successfully treated by GSTP1 according to the present invention. This may be important for farm or zoo animals (especially breeding farm animals, such as (former) racing horses) or pets, for example dogs, cats and horses.

Although the present invention is also useable for the prevention of CMP and IHD it is clear that the primary focus of the present invention lies in the treatment of human CMP and IHD patients who have already been diagnosed of CMP or IHD or which have a high risk of developing CMP or IHD, for example patients with hypertension (e.g. Stage 2 patients with systolic pressure of 160 mm Hg or more and/or with diastolic pressure of 100 mm Hg or more). Another preferred embodiment of the preventive aspect of the present invention is for angina pectoris patients, whereby myocardial infarction might or might not have occurred in this set of patients; and heart insufficiency or heart failure (Mc Murray et al., Lancet 365 (2005), 1877-1889) may or may not be present. Here, even continuous intravenous administration or continuous administration to the heart muscle is indicated.

Preferred routes of administration of the GSTP1 containing medicament according to the present invention are parenteral routes, preferably intraperitoneal or intravenous administration, intravenous administration being specifically preferred. Intravenous administration can be performed e.g. via bolus injection or by continuous intravenous delivery over a longer time period (e.g. 30 min to 6 h, especially 1 to 3 h). In the process of heart surgery also administration directly to the heart (intramyocardial injection) is preferred. With this route, GSTP1 activity can be directly and in high concentrations delivered to the area of need, e.g. to an infarct region. Another preferred route of administration is administration to the coronary sinus (e.g. via a catheter inserted into the coronary sinus). Oral or mucosal routes (although described for GSTP1 in principle; see e.g. U.S. Pat. No. 5,976,528 A) are less preferred, since GSTP1 is a protein and for this route specific protection measures (enteric coating, encapsulation, etc.) are necessary as well as a significant optimisation with respect to galenic manufacture.

Preferred dosages for administration are dosages of 0.001 to 100 mg GSTP1/kg, preferably 0.01 to 10 mg GSTP1/kg, especially 0.1 to 1 mg GSTP1/kg, to a human individual, preferably via intravenous administration; or dosages of 0.1 to 10000 U GSTP1/kg, preferably 1 to 1000 U GSTP1/kg, especially 10 to 100 U GSTP1/kg, to a human individual, preferably via intravenous administration. These are preferred daily dosages for intravenous application ("kg" means kg body weight of the person to be treated). During surgery, these dosages may also be applied, either as a whole or even more than one dosage; or only part of the dosage (having in mind that the GSTP1 can directly be applied during surgery in the area needed). "Ready-to-use" daily dosage forms (e.g. for a 80 kg and/or a 60 kg human individual) can be pre-manufactured and can be made storage-stable by lyophilisation or freezing (and keeping at e.g. −20° C.). The dosage can then be fully or only partially consumed (e.g. based on the body weight of the person to be treated).

GSTP1 according to the present invention is also referred to as "GSTP1-1", "GST class-pi", "DFN7", "GST3", "GST π", etc. and conjugates reduced glutathione to a wide number of exogenous and endogenous hydrophobic electrophiles (EC 2.5.1.18; Catalytic activity: RX+glutathione=HX+R—S-glutathione). The human sequence (Seq. ID. No. 1) is listed as "GSTP1_HUMAN, P09211" in the UniProtKB/SwissProt database (HGNC: 4638, Entrez Gene: 2950).

Orthologs from mammals are known, e.g. from chimpanzee (Pan troglodytes; NCBI accessions: 745954, XM_001152516.1, XP_001152516.1) and mouse (Mus musculus; NCBI accessions: 148701, NM_013541.11, NP_038569.11, AK0791445, BC0020485), but also from non-mammals, such as zebrafish (Danio rerio) and worm (Caenorhabditis elegans).

The present invention also relates to a pharmaceutical composition comprising GSTP1, preferably human recombinant GSTP1 or human placenta GSTP1, and a pharmaceutically acceptable carrier for the prevention or treatment of cardiomyopathies or ischemic heart diseases.

According to a preferred embodiment, the composition according to the present invention contains 1 to 100000 U GSTP1, preferably 10 to 10000 U GSTP1, especially 10 to 1000 U GSTP1. A unit of GSTP1 activity conjugates 1.0 micro-mole of 1-chloro-2,4-dinitrobenzene with reduced glutathione per minute at pH 6.5 at 25° C.

A preferred composition according to the present invention also contains a buffer. Typical buffer systems are the carbonic acid/$HCO_3$ system (pH 6.2 to 8.6; neutral), carbonic acid/silicate buffer (pH 5.0 to 62; weakly acidic), acetic acid/acetate buffer (pH 3.7 to 5.7), phosphate buffer ($NaH_2PO_4$+ $Na_2HPO_4$; pH 5.4 to 7.8), ammonia buffer ($NH_3$+$H_2O$+ $NH_4Cl$; pH 8.2 to 10.2), TRIS/HCl (Tris(hydroxymethyl)-aminomethane; pH 7.2 to 9.0), HEPES (4-(2-Hydroxyethyl)-1-piperazinethanesulfonic acid; pH 6.8 to 8.2), HEPPS (4-(2-Hydroxyethyl)-piperazine-1-propane sulfonic acid; pH 7.3 to 8.7) or MES (2-(N-Morpholino)ethanesulfonic acid; pH 5.2 to 6.7). Preferred buffers according to the present invention is a phosphate buffer, a Tris-HCl buffer or a HEPES buffer, with a pH of 5.5 to 9.0, preferably of 6.0 to 8.5, especially of 6.5 to 8.0. Buffer concentrations can preferably be adjusted to 1 mM

```
SEQ. ID. NO. 1:
  1 mppytvvyfp vrgrcaalrm lladqgqswk eevvtvetwq egslkascly gqlpkfqdgd 61 ltlyqsntil rhlgrtlgly gkdqqeaalv dmvndgvedl rckyisliyt nyeagkddyv 121 kalpgqlkpf etllsqnqgg ktfivgdqis fadynlldll lihevlapgc ldafpllsay 181 vgrlsarpkl kaflaspeyv nlpingngkq
```

Several variants exist for this human protein (homozygous as well as heterozygous), the most important variants are a Ile to Val exchange at position 105 and a Ala to Val exchange at position 114 (Melen et al., 2008). Other variants include a Gly to Glu exchange at position 78, a Thr to Ser exchange at position 110, a Gly to Glu exchange at position 139, a Asp to Tyr exchange at position 147 and a Asp to His exchange at position 158. Several other SNPs are known without affecting the amino acid sequence.

If the CMP or IHD patient to be treated with GSTP1 according to the present invention has such an allele which results in a (heterozygous or homozygous) amino acid exchange compared to SEQ.ID.No. 1, it may be recommendable to administer to such a patient the allelic form of this protein. This is specifically preferred for patients who are homozygous for this allele, e.g. patients with homozygous 105Val or 114Val allele (who could then receive the 105Val or 114Val GSTP1 variant, respectively). In such cases, the risk of developing adverse reactions, especially adverse immune reactions (which is always a topic for proteinaceous medicaments), is kept low. Anyway, any ingredients in the pharmaceutical preparation containing GSTP1 according to the present invention eliciting or boosting an immune reaction in the patient should be kept at minimum if possible.

to 1 M, especially 10 mM to 0.5 M. Other preferred additional ingredients include stabilisers, chelators, salts, etc., such as glycerol, glucose, saccharose, maltose, EDTA or similar substances, NaCl, KCl, $NH_4Cl$ and similar salts usable in pharmaceutical preparations. Of course, all ingredients in a pharmaceutical preparation have to be of pharmaceutical grade quality.

Pharmaceutically acceptable carriers preferably used are physiological saline, vegetable oils, mineral oil, aqueous sodium caroboxymethyl cellulose or aqueous polyvinylpyrrolidone; however, also sterile water can be used.

GSTP1 to be used according to the present invention can be provided by various ways. As mentioned above, GSTP1 from human placenta is one of the preferred natural sources of GSTP1. Other preferred sources are cultures of GSTP1 (over-)expressing cells. GSTP1 preparations are also commercially available. The preferred industrial production route according to the present invention is, however, recombinant production of GSTP1. Recombinant production of GSTP1 is well established, as well as its purification from such sources (e.g. Luo et al., 2009, Wu et al., 2006; WO 98/21359 A1; U.S. Pat. No. 5,976,528; etc.). Expression vectors (e.g. WO 98/21359 A1, Part D (pages 40 to 51) containing the GSTP1 coding sequences are transferred in suitable host cells (such as COS, HEK 293, HeLa, VERO, W138, BHK or MDCK cells, but also yeast, plant, insect and bacterial cells (*S. cerevisiae, E. coli*, etc.). GSTP1 is then expressed and purified according to standard methods. Recombinant GSTP1 production may also use variant forms of GSTP1 with additional sequences which facilitate purification, such as metal chelating peptides, protein A domains, affinity purification tags, etc. (e.g. U.S. Pat. No. 5,976,528 A, column 16). Such variants can—after purification or in the course of purification—be removed e.g. via cleavable linker sequences (protease, entereokinase, etc.). Purified batch preparations of GSTP1 may contain e.g. 1 to 200 U GSTP1 activity per mg total protein. Preferred pharmaceutical GSTP1 compositions contain 5 to 200 U/mg protein, especially 10 to 150 U/mg protein. The pharmaceutical preparation according to the present invention is always provided as an appropriately labelled product which is sterile and useable for administration to human patients according to the present invention.

According to another aspect, the present invention relates to GSTP1 as a diagnostic target for CMP or IHD. The present invention provides the use of GSTP1 for the diagnosis of CMP or IHD. Although GSTP1 is a known and established marker in tumor diagnosis, it was surprising that GSTP1 is a biomarker for CMP or IHD which is even superior to the current "gold standard", pro-BNP, with respect to sensitivity and specificity.

The cardiomyopathies or ischemic heart diseases referred to above for therapeutical use of GSTP1 can also be diagnosed according to the present invention.

The present invention therefore relates to a method for diagnosing CMP or IHD, especially the indications mentioned above, by determining the amount of GSTP1 or GSTP1 mRNA in a biological sample and comparing this amount to the GSTP1 or GSTP1 mRNA amount in a biological sample with a defined and known CMP/IHD status, especially from a healthy human individual or a patient. This comparison can be done practically, i.e. in that a real sample is tested in the same manner as the biological sample (side-by-side), it can also be a virtual comparison so that the determined value is compared with a known value of a healthy or diseased sample.

Preferred techniques for determining the amount of GSTP1 include antibody-liked techniques, such as ELISA, optionally combined with electrophoresis techniques or radio immunoassay (RIA). Electrophoresis techniques may also be combined with MALDI techniques.

Alternatively, GSTP1 mRNA may be determined, e.g. by quantitative real time RT-PCR.

The preferred diagnosis target is a human patient who is suspected to have CMP or IHD, a human patient who is at risk for developing CMP or IHD or a human patient who has CMP or IHD (who has to be monitored for progression of the disease).

Preferred biological samples according to the present invention include human blood, plasma or serum samples or human myocardial biopsy samples. These samples can also be tested by routine methods.

Typically, a high concentration of GSTP1 in serum is indicative of CMP or IHD. In healthy persons, serum concentrations of GSTP1 are below 50 ng/ml or, preferably, even below 10 ng/ml. A CMP or IHD diseased status can be diagnosed at a serum level at 50 ng/ml or above, preferably at 100 ng/ml or above. Severe forms of CMP or IHD can be diagnosed at 200 ng/ml or above. Of course, these levels always depend on the technique used for as-saying the GSTP1 protein. Alternatively, CMP or IHD diseased status can be diagnosed if the serum level of GSTP1 is elevated by at least the factor 2, preferably by at least the factor 5, compared to a healthy status, especially the healthy status of the same patient. Severe forms could be diagnosed, if the serum GSTP1 level is elevated by at least the factor 10, especially by at least the factor 20, compared to a healthy status, especially the healthy status of the same patient.

With the present invention determining the amount of GSTP1 or GSTP1 mRNA in a sample can be performed within a very short time by standard test methods, such as ELISA or PCR. Based on the DNA and amino acid sequence according to SEQ.ID.NO.2

```
atgccgccct acaccgtggt ctatttccca gttcgaggcc gctgcgcggc cctgcgcatg   60
ctgctggcag atcagggcca gagctggaag gaggaggtgg tgaccgtgga gacgtggcag  120
gagggctcac tcaaagcctc ctgcctatac gggcagctcc ccaagttcca ggacggagac  180
ctcaccctgt accagtccaa taccatcctg cgtcacctgg gccgcaccct tgggctctat  240
gggaaggacc agcaggaggc agccctggtg gacatggtga atgacggcgt ggaggacctc  300
cgctgcaaat acgtctccct catctacacc aactatgagg cgggcaagga tgactatgtg  360
aaggcactgc ccgggcaact gaagccttt gagaccctgc tgtcccagaa ccagggaggc  420
aagaccttca ttgtgggaga ccagatctcc ttcgctgact acaacctgct ggacttgctg  480
ctgatccatg aggtcctagc ccctggctgc ctggatgcgt tccccctgct ctcagcatat  540
gtggggcgcc tcagcgcccg gcccaagctc aaggccttcc tggcctcccc tgagtacgtg  600
aacctcccca tcaatggcaa cgggaaacag tga                              633
``` and SEQ.ID.NO.1 (and the data base entries mentioned above for the GSTP1 gene and the GSTP1 protein), the present invention also provides e.g. a PCR assay for identification of *S. aureus* infections or a sandwich ELISA assay. In a suitable ELISA according to the present invention, GSTP1 can be caught out of a biological sample with a GSTP1-specific antibody and detected and quantified with a second antibody directed against a different epitope of GSTP1 or an antibody being specific for the previous binding event.

Detection of GSTP1 transcripts (m-RNA) is possible by standard quantitative nucleic acid tests, such as quantitative RT-PCR. The present invention therefore also provides a kit for determining the amount of GSTP1 mRNA in a least two synthetic nucleic acid sequences for amplifying at least one nucleic acid sequence encoding GSTP1 or parts thereof, wherein at least of one of the synthetic nucleic acid sequences in the kit is selected from the group consisting of: (a) a suitable primer pair, the primers being a nucleic acid sequence comprising 10-30 consecutive nucleotides of at least one of the following: (i) the GSTP1 mRNA according to SEQ.ID.NO.2 or the complementary sequence thereof; or (ii) from the 5' or 3' noncoding region of the GSTP1 gene (e.g. in regions extending up to 500, preferably up to 200, especially up to 100, nucleotides into the 5'- or 3-direction or complementary sequences thereof; such sequences are present in the sequence library entries mentioned above); said primers being usable for polymerising a nucleotide sequence located between the primers on the GSTP1 gene or its 5'- or 3'-region (said polymerizable GSTP1 nucleotide sequence being PCR detectable and preferably up to 1000 bp, more preferred up to 500 bp, even more preferred up to 300 bp in length; on the other hand, the primers may also be selected to polymerise (with PCR) the whole GSTP1 m-RNA); and (b) suitable reagents for a polymerase chain reaction (PCR). Preferably, the kit further comprises: (c) instructions for use and (d) optionally, a positive and/or negative control for determining and/or quantification of GSTP1 mRNA, especially a control nucleic acid encoding GSTP1 or a fragment thereof. Examples of suitable PCR reagents include PCR reaction buffer, $Mg^{2+}$ (e.g., $MgCl_2$), dNTPs, DNA polymerases (such as reverse transcriptases and thermostable DNA polymerases (e.g., Taq-related DNA polymerases and Pfu-related DNA polymerases)), RNase, PCR reaction enhancers or inhibitors, PCR reaction monitoring agents (e.g., double-stranded DNA dye (such as SYBR™ Green), TaqMan™ probes, molecular beacons, and Scorpions™), and PCR-grade water.

The primers described herein are particularly useful in a polymerase chain reaction (PCR) assay. PCR is a practical system for in vitro amplification of a DNA base sequence. For example, a PCR assay may use a heat-stable polymerase and two about 10 to 30 base primers: one complementary to the (+)-strand at one end of the sequence to be amplified, and the other complementary to the (−)-strand at the other end. Because the newly-synthesized biological sample, comprising: (a) a primer set comprising at DNA strands can subsequently serve as additional templates for the same primer sequences, successive rounds of primer annealing, strand elongation, and dissociation may produce rapid and highly-specific amplification of the desired sequence. PCR also may be used to detect the existence of a defined sequence in a GSTP1 m-RNA containing sample.

By way of example, a typical PCR assay according to the present invention might start—optionally after reverse transcription of the mRNA into DNA—with two synthetic oligonucleotide primers which are specifically and complementarily binding to two regions of the target DNA or its complementary strand, respectively, encoding GSTP1 or its 5'- and/or 3' region (one for each strand) that is to be amplified. These may be added to the target DNA (that needs not be pure) in the presence of excess deoxynucleotides (dNTPs) and a thermostable DNA polymerase (e.g., Taq polymerase). In a series (typically 20-40) of temperature cycles, the target DNA may be repeatedly denatured (about 80-100° C., e.g. 90° C.), annealed to the primers (typically at 40-65° C.), and a daughter strand may be extended from the primers (typically at 65-80° C., e.g. 72° C.). As the daughter strands themselves act as templates for subsequent cycles, DNA fragments matching both primers are amplified exponentially, rather than linearly. The target DNA needs be neither pure nor abundant; thus, PCR is specifically suitable in the clinical diagnostics according to the present invention.

These tests may preferably employ labels which are also suitable for quantification, such as biotin, fluorescent molecules, radioactive molecules, chromogenic substrates, chemiluminescence markers, and the like. The methods for biotinylating nucleic acids are well known in the art, as are methods for introducing fluorescent molecules and radioactive molecules into oligonucleotides and nucleotides. Detection methods are well known for fluorescent, radioactive, chemiluminescent, chromogenic labels, as well as other commonly used labels. Briefly, chemiluminescence can be identified and quantitated most directly by their emission wavelengths and intensity. When biotin is employed, it is detected by avidin, streptavidin or the like, which is conjugated to a detectable marker, such as an enzyme (e.g. horseradish peroxidase). Steptavidin binds with high affinity to biotin, unbound streptavidin is washed away, and the presence of horseradish peroxidase enzyme is then detected using a luminescence-emission substrate in the presence of peroxide and appropriate buffers.

Determining the amount of GSTP1 in a sample preferably includes ELISA, RIA and FACS. Detection and quantification of GSTP1 by using anti GSTP1 antibodies is well established in the art (especially in tumor medicine) and can be readily applied for the purpose of diagnosing CMP or IHD according to the present invention (e.g. WO 98/21359 A1 ("F. Antibodies"); U.S. Pat. Nos. 5,976,528 A, 5,427,917 A). Normal or standard values for GSTP1 expression are established by combining body fluids or cell extracts taken from normal mammalian subjects, preferably human, with antibody to GSTP1 under conditions suitable for complex formation. The amount of standard complex formation may be quantified by various methods, preferably by photometric means. Quantities of GSTP1 expressed in subject, samples, control and disease, from biopsied tissues are compared with the standard values. Deviation between standard and subject values establishes the parameters for diagnosing disease. As already stated above, most preferred samples are of human heart biopsies and samples derived from human blood of individual human patients having CMP or IHD, being suspected of having CMP or IHD or being at risk of developing CMP or IHD.

The present invention is further illustrated by the following examples and the drawing figures, yet without being restricted thereto.

FIG. 1 shows increased GSTP1 and TRAF2 in DCM and ICM patients. (A) Representative gene array images show increased hybridization to GSTP1 and TRAF2 array sequences (arrows) of labelled cDNA probes. (B) Representative protein array images demonstrating enhanced Cy5 (red) staining for cardiac GSTP1 and TRAF2 proteins in DCM and ICM patients compared to the Cy3 (green) staining of controls. (C) Quantification of myocardial GSTP1 and TRAF2 mRNA expressions by real time RT-PCR. GSTP1 (*P<0.0001) and TRAF2 (P<0.0001) mRNA expression is significantly up-regulated in heart failure patients compared to controls. (D) Representative Western blot images and quantification of myocardial GSTP1 and TRAF2 protein expressions corrected for protein loading control levels. Myocardial protein expression levels were elevated in DCM and ICM for GSTP1 (P<0.0001, P=0.0019) and TRAF2 (P<0.0001, P=0.005) as compared to controls. No significant differences were found in GSTP1 mRNA and protein expression when DCM and ICM were compared; although TRAF2 mRNA (†P=0.001) and protein (†P≤0.0001) expression levels were significantly higher in DCM as compared to ICM. *, significantly different versus controls.

Figure 2:
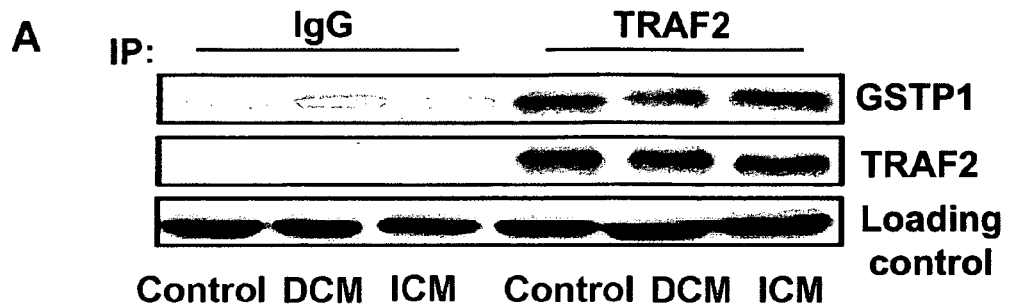
Figure 2:
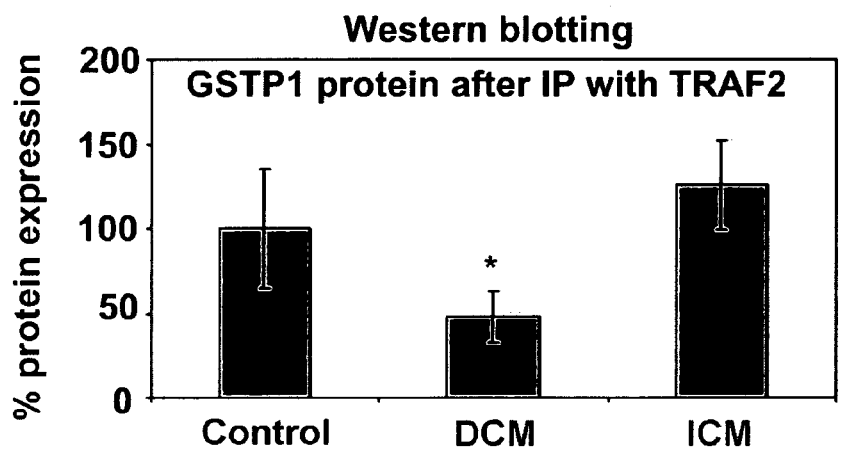
Figure 2:
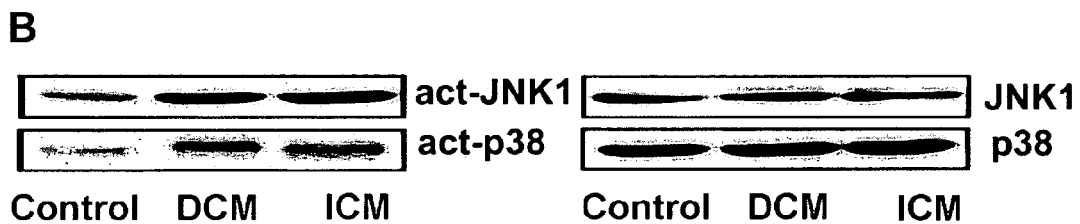
Figure 2:
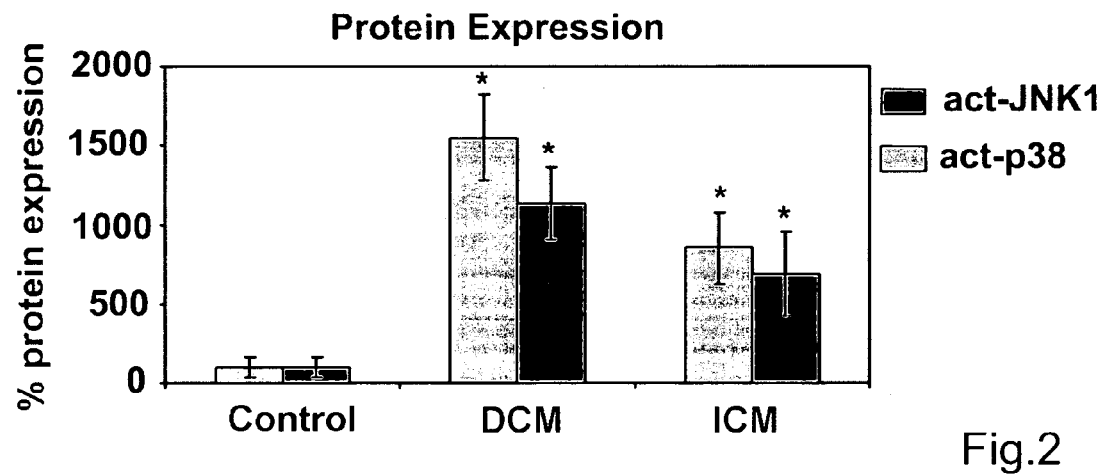

FIG. 2 shows GSTP1-TRAF2 interaction and activation of JNK and p38 in DCM and ICM. (A) Representative Western blot images and quantification of myocardial GSTP1-TRAF2 complex formation in DCM, ICM and controls. LV myocardial lysates were immunoprecipitated (IP) and precipitates were analyzed on Western blotts. Significantly lower GSTP1-TRAF2 association was found in DCM compared to ICM and controls (*$P \leq 0.008$). (B) Representative Western blot images and quantification of myocardial active JNK1 and p38 protein expression in DCM, ICM and controls. In both DCM and ICM cardiac protein expression of active JNK as well as p38 ($P < 0.0001$) is significantly upregulated as compared to controls. Moreover, DCM patients reveal a significantly higher cardiac JNK and p38 protein expression (†$P < 0.0001$) as compared to ICM. All protein expressions were corrected for protein loading control levels. *, significantly different versus control.

Figure 3:
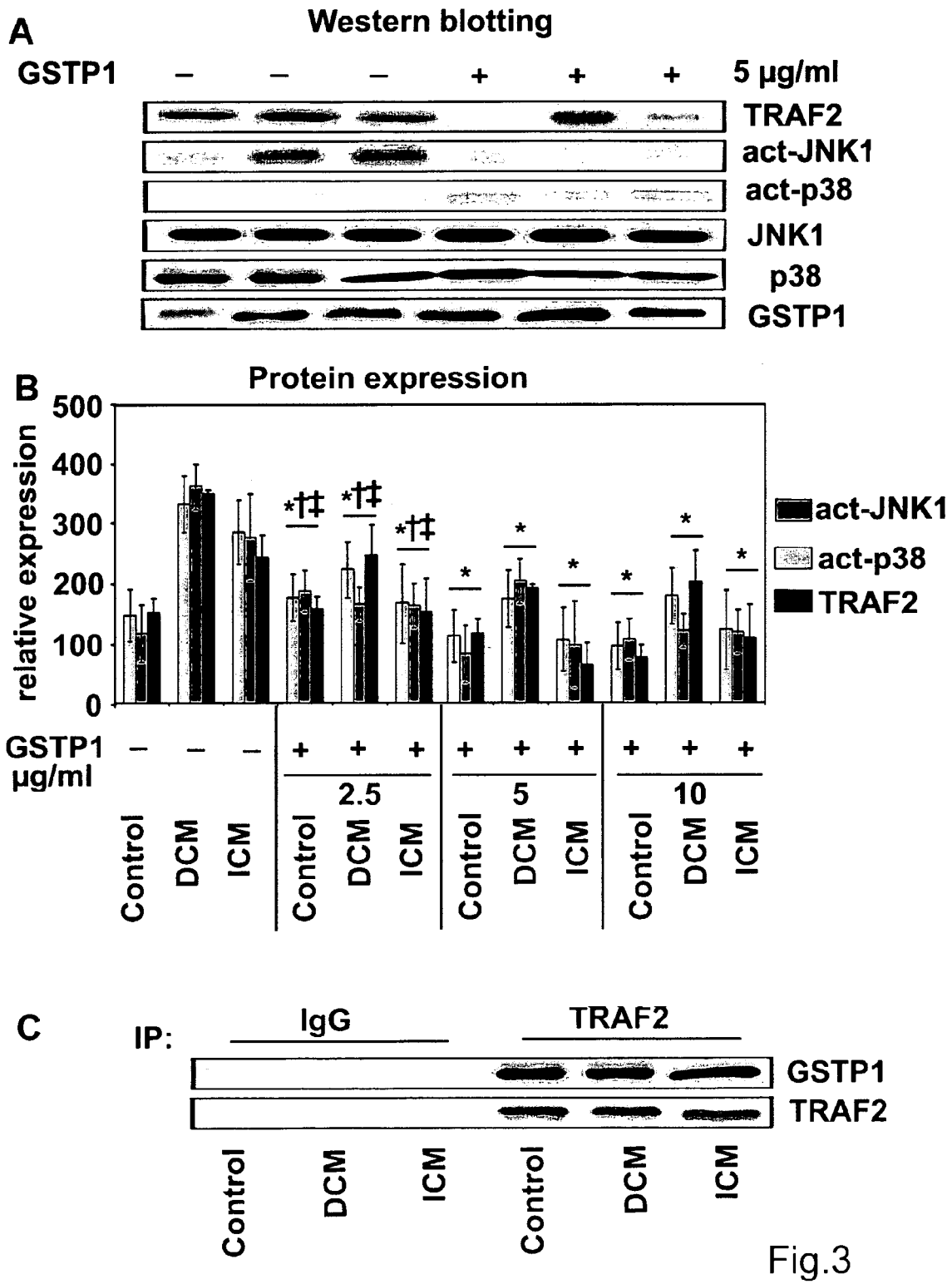
Figure 4:
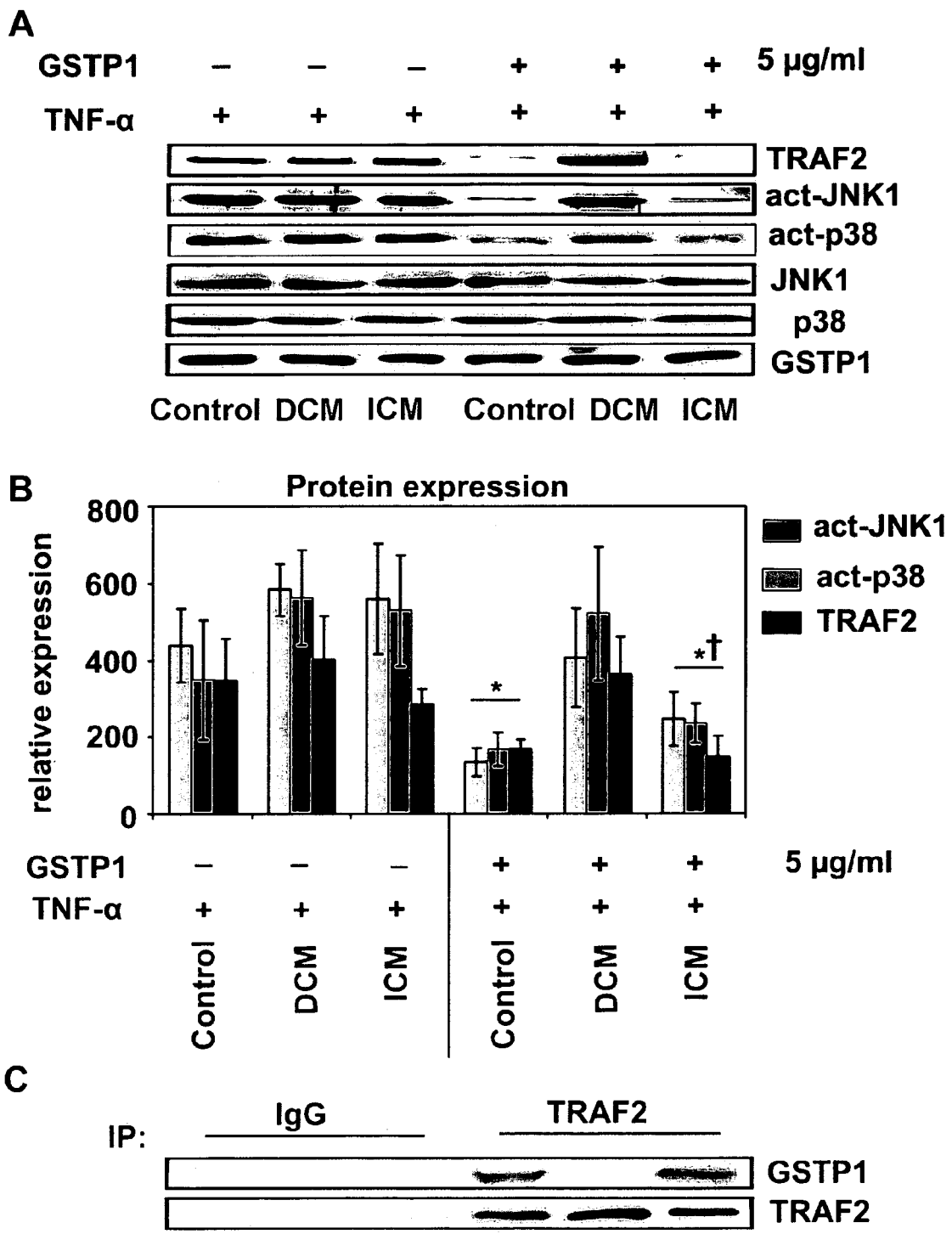

FIG. 3 shows that GSTP1 modulates cardiac TRAF2-JNK1/p38 system in cardiac tissue cultures. (A) Representative Western blot images of TRAF2, GSTP1, active JNK and active p38 protein expressions in cardiac tissue cultures treated with 5 µg/mL recombinant GSTP1. (B) Quantification of TRAF2, active JNKs and active p38 protein expressions in DCM, ICM and control cardiac tissue cultures treated with recombinant GSTP1 (2.5, 5, 10 µg/ml) for 24 h. Protein expressions of TRAF2 was significantly reduced compared to untreated ones dependent on the concentration used (DCM: $P=0.011$ for 2.5 µg/mL, $P=0.014$ for 5 µg/mL, $P=0.003$ for 10 µg/mL; ICM: $P=0.006$ for 2.5 µg/mL, $P=0.003$ for 5 µg/mL, $P=0.0001$ for 10 µg/mL; controls: $P=0.19$ for 2.5 µg/mL, $P=0.0003$ for 5 µg/mL, $P=0.03$ for 10 µg/mL). Following GSTP1 treatment, active JNK expression declined in DCM, ICM and control cardiac tissue compared to untreated group dependent on the concentration used (DCM: $P=0.0009$ for 2.5 µg/mL, $P=0.01$ for 5 µg/mL, $P=0.0003$ for 10 µg/mL; ICM: $P=0.0005$ for 2.5 µg/mL, $P=0.007$ for 5 µg/mL, $P<0.0001$ for 10 µg/mL; controls: $P=0.001$ for 2.5 µg/mL, $P=0.69$ for 5 µg/mL, $P=0.71$ for 10 µg/mL). Likewise, active p38 expression decreased in response to GSTP1 treatment in DCM, ICM and control cardiac tissue compared to untreated ones dependent on the concentration used (DCM: $P=0.004$ for 2.5 µg/mL, $P<0.0001$ for 5 µg/mL, $P=0.0009$ for 10 µg/mL; ICM: $P=0.03$ for 2.5 µg/mL, $P=0.0001$ for 5 µg/mL, $P=0.008$ for 10 µg/mL; controls: $P=0.008$ for 2.5 µg/mL, $P=0.0004$ for 5 µg/mL and µg/mL). The comparison of the applied GSTP1 concentrations with regard to TRAF2, JNK and p38 reduction indicated that in DCM and ICM but not controls the differences between 2.5 µg/mL and 5 µg/mL as well as 10 µg/mL were significant. TRAF2: (DCM: $P=0.01$ for 2.5 vs. 5 µg/mL and vs. 10 µg/mL, $P=0.62$ for 5 vs. 10 µg/mL; ICM: $P=0.0007$ for 2.5 vs. 5 µg/mL, $P=0.0004$ for 2.5 vs. 10 µg/mL, $P=0.35$ for 5 vs. 10 µg/mL; control: $P=0.07$ for 2.5 vs. 5 µg/mL, $P=0.06$ for 2.5 vs. 10 µg/mL, $P=0.15$ for 5 vs. 10 µg/mL). JNK: (DCM: $P=0.0006$ for 2.5 vs. 5 µg/mL, $P=0.003$ for 2.5 vs. 10 µg/mL, $P=0.48$ for 5 vs. 10 µg/mL; ICM: $P=0.004$ for 2.5 vs. 5 µg/mL, $P=0.01$ for 2.5 vs. 10 µg/mL, $P=0.88$ for 5 vs. 10 µg/mL; control: $P=0.02$ for 2.5 vs. 5 µg/mL, $P=0.05$ for 2.5 vs. 10 µg/mL, $P=0.97$ for 5 vs. 10 µg/mL). p38 (DCM: $P=0.0002$ for 2.5 vs. 5 µg/mL, $P=0.04$ for 2.5 vs. 10 µg/mL, $P=0.76$ for 5 vs. 10 µg/mL; ICM: $P=0.0006$ for 2.5 vs. 5 µg/mL, $P=0.02$ for 2.5 vs. 10 µg/mL, $P=0.41$ for 5 vs. 10 µg/mL; control: $P=0.06$ for 2.5 vs. 5 µg/mL, $P=0.08$ for 2.5 vs. 10 µg/mL, $P=0.29$ for 5 vs. 10 µg/mL). (C) Representative Western blot images of myocardial GSTP1-TRAF2 complexes from DCM, ICM and controls cardiac tissue cultures treated with recombinant GSTP1 (5 µg/ml) and subjected to immunoprecipitation (IP). GSTP1-treated cardiac tissue cultures association between GSTP1 and TRAF2 was dose and disease-independent and significantly higher ($P=0.02$ for 5 µg/mL GSTP1 concentration; results for 2.5 and 10 µg/mL GSTP1 concentration not shown) as compared to untreated samples. *, significantly different versus control. †, significantly different versus GSTP1 2.5 µg/ml treated tissue cultures. ‡, significantly different versus GSTP1 5 µg/ml and 10 µg/ml treated tissue FIG. 4 shows that TNF-α abrogates sensitivity of TRAF2-JNK1/p38 cascade to GSTP1 in DCM cardiac cultures. (A) Representative Western blot images and quantification (B) of DCM, ICM and control cardiac tissue cultures treated with TNF-α (50 ng/ml) and GSTP1 (5 µg/ml). TNF-α-activated JNK ($P=0.08$) and p38 ($P=0.75$) cascade as well as TRAF2 ($P=0.18$) protein expression were not affected by recombinant GSTP1 in DCM cardiac tissue cultures. In ICM and controls active JNK ($P<0.001$; $P<0.002$), active p38 ($P<0.0002$; $P<0.0001$) and TRAF2 ($P<0.001$; $P=0.003$) protein expressions was markedly reduced in response to GSTP1 stimulation. The comparison of the GSTP-treated ICM and DCM cardiac tissue cultures indicate significantly lower TRAF2, actives JNK and p38 (†$P<0.001$) protein expressions in ICM as compared to those of DCM. (C) Representative Western blot images of immunoprecipitated cardiac tissue lysates treated with TNF-α (50 ng/ml) and GSTP1 (5 µg/ml). The failure of GSTP1 to associate with TRAF2 following TNF-α stimulation in DCM cardiac tissue was present in contrast to ICM and control cardiac tissue.

Figure 5:
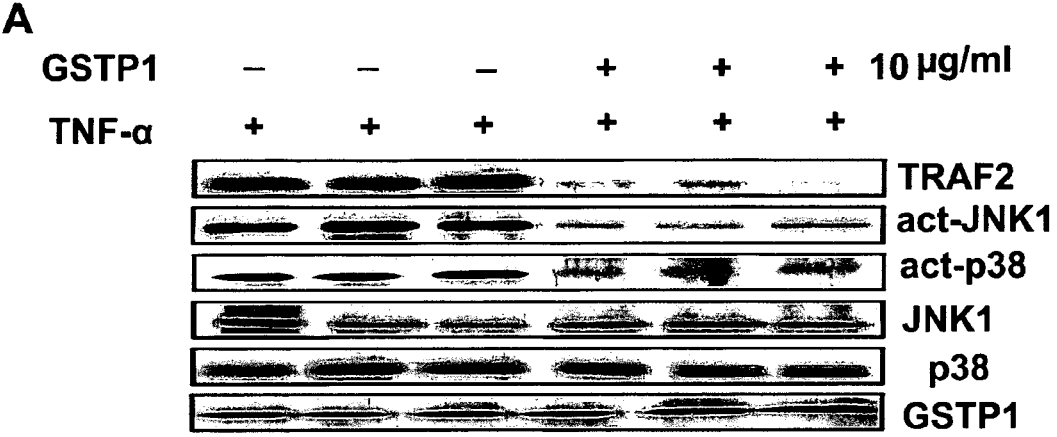
Figure 5:
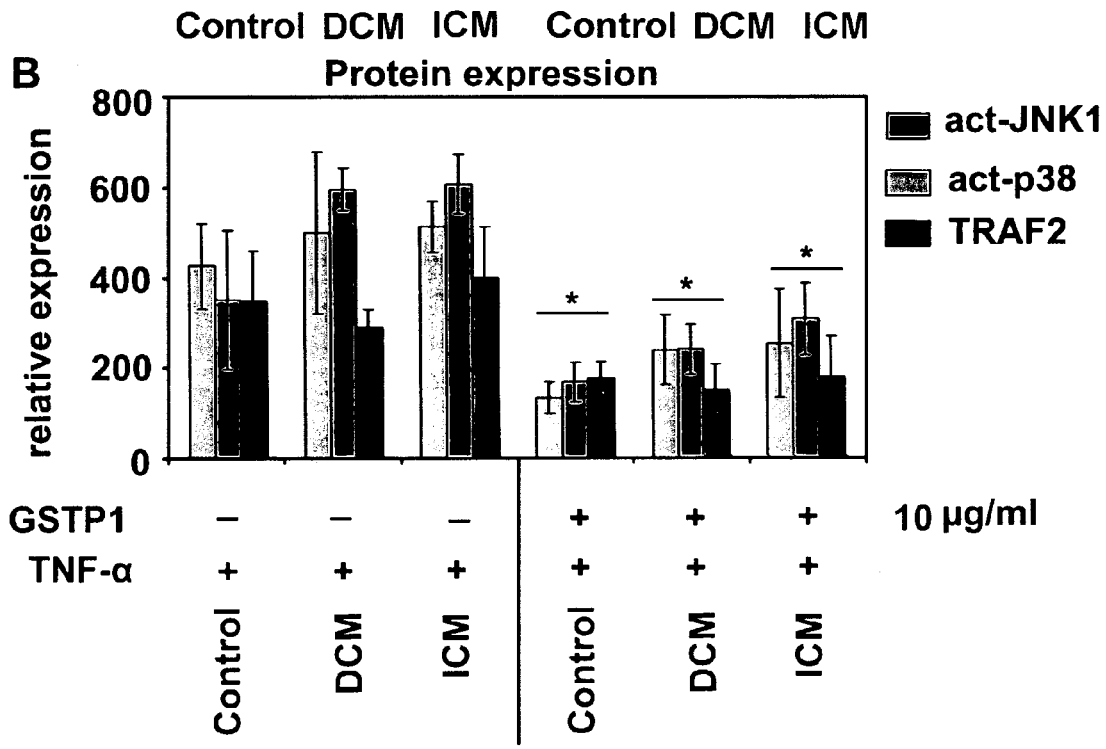
Figure 5:
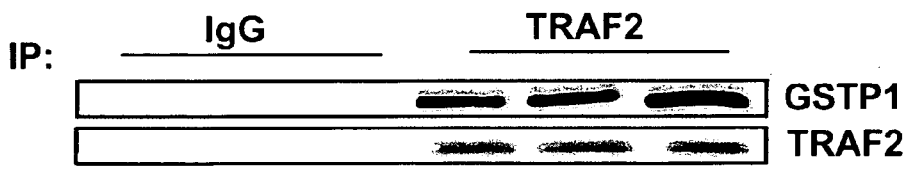

FIG. 5 shows that higher GSTP1 concentrations rescue TRAF2-mediated JNK1/p38 downregulation following TNF-α treatment. (A) Representative Western blot images and quantifications (B) of DCM, ICM and control cardiac tissue cultures treated with TNF-α (50 ng/ml) and GSTP1 (10 µg/ml). (B) The results demonstrate that DCM cardiac tissue cultures treated with GSTP1 at 10 µg/mL and TNF-α express markedly reduced JNK and p38 activation as well as reduced TRAF2 protein expression (*$P<0.0001$) as compared to TNF-α-treated controls. (C) The immunoprecipitates of DCM cardiac tissue lysates demonstrate significant ($P \leq 0.035$) increase of GSTP1-TRAF2 association at 10 µg/ml GSTP1 as compared to 5 mg/ml GSTP1.

Figure 6:
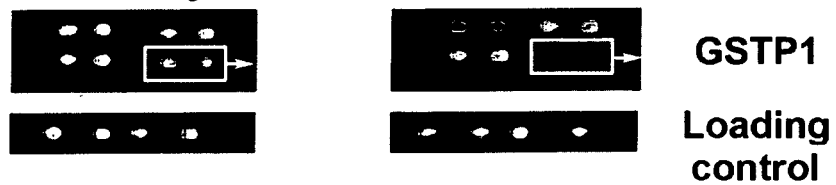
Figure 6:
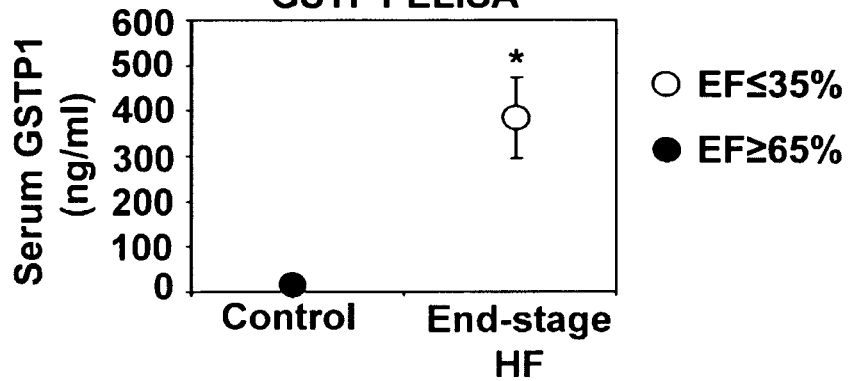
Figure 6:
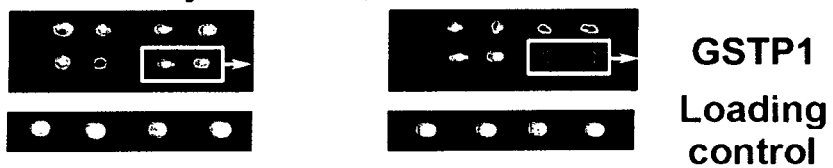
Figure 6:
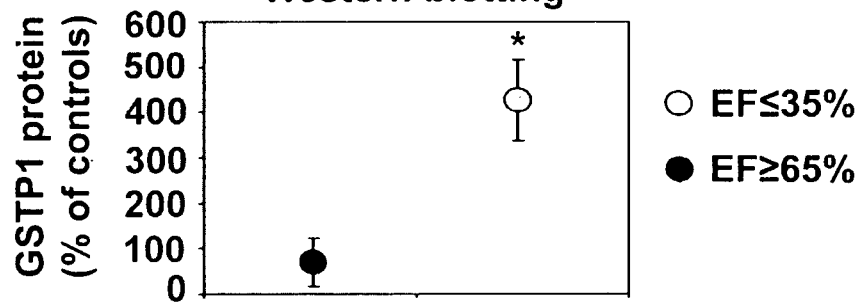

FIG. 6 shows that serum and cardiac GSTP1 is associated with CMP. (A) Representative serum protein array images demonstrate enhanced Cy3 (green) and Cy5 (red) staining for serum GSTP1 protein in end-stage heart failure (HF) (EF$\leq$35%; n=40) patients compared to controls (EF$\geq$65%; n=40). (B) ELISA measurements indicate significant (*$P<0.0001$) elevation of serum GSTP1 concentration in end-stage HF patients with (EF$\leq$35%; n=40) versus controls with (EF$\geq$65%; n=40). (C) Representative cardiac tissue protein array images demonstrate enhanced Cy3 (green) and Cy5 (red) staining for cardiac GSTP1 protein in end-stage HF patients (EF$\leq$35%; n=40) compared to controls (EF$\geq$65%; n=20). (D) Representative Western blotting images and quantification of myocardial GSTP1 protein expression corrected for protein loading control levels. GSTP1 protein levels were significantly elevated in end-stage HF patients with EF$\leq$35% versus control cardiac graft tissue (*$P \leq 0.001$).

Figure 7:
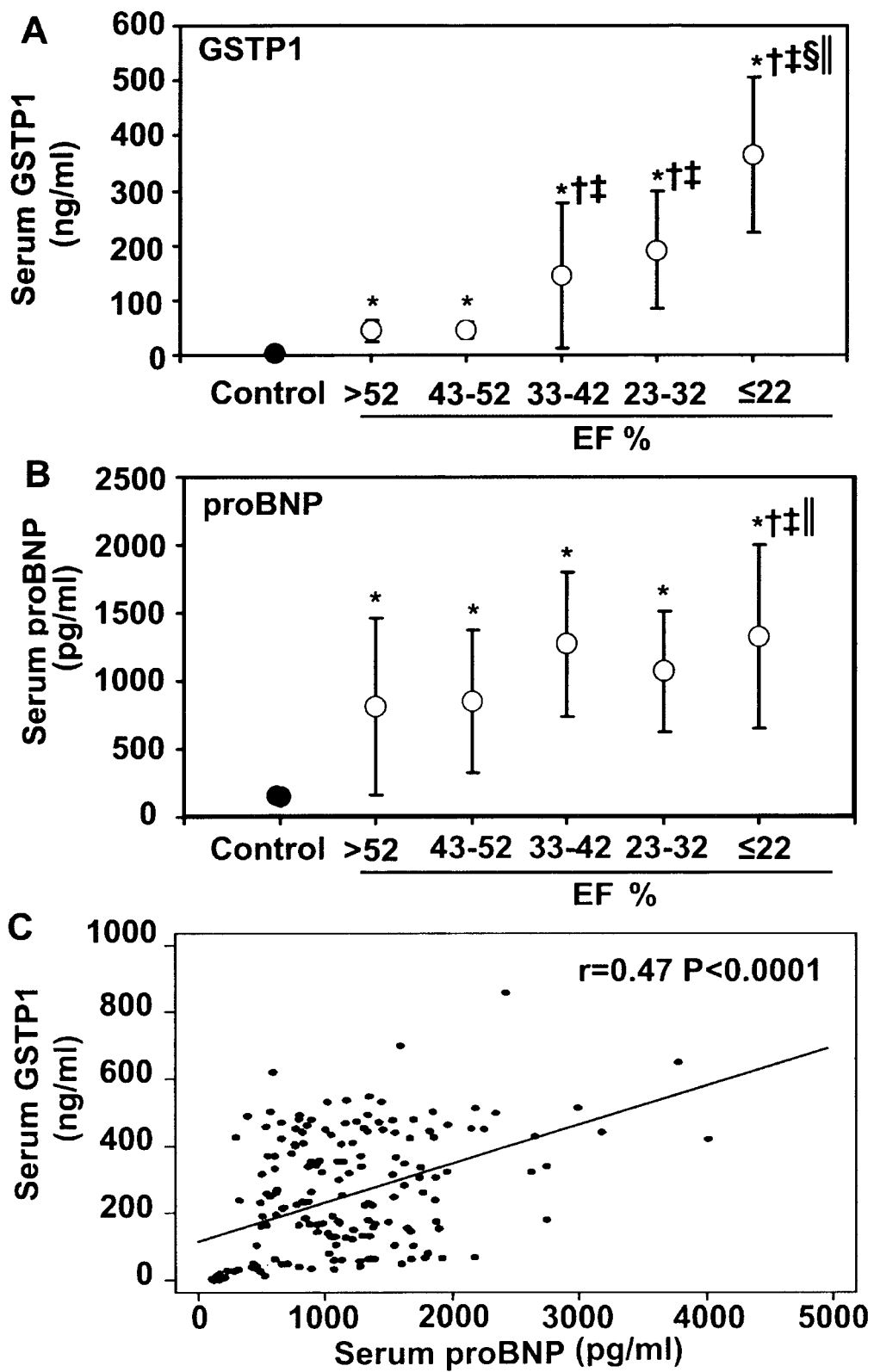

FIG. 7 shows serum GSTP1 and proBNP association with ejection fraction (EF) and the correlation between GSTP1 and proBNP. (A) Heart failure patients with EF$\leq$22% have significantly higher serum GSTP1 concentrations as compared to all other EF groups. Patients with EF33-42%, EF23-32% and EF$\leq$22% have significantly higher serum GSTP1 concentration as compared to those with EF>52% and EF 43-52%. (B) Patients with EF$\leq$22% have significantly higher serum proBNP concentration as compared to all other EF groups. No significant differences in serum proBNP were observed between all other EF groups. (C) Correlation plot of serum GSTP1 and serum proBNP measurements for all study subjects. Significant positive relationship was noted between serum GSTP1 and proBNP (r=0.47; P<0.0001). *P<0.001 versus control, †P<0.0001 versus EF>52%, ‡P<0.0001 versus EF 43-52%, §P<0.0001 versus EF 33-42%, ‖P<0.0001 versus EF 23-32%.

Figure 8:
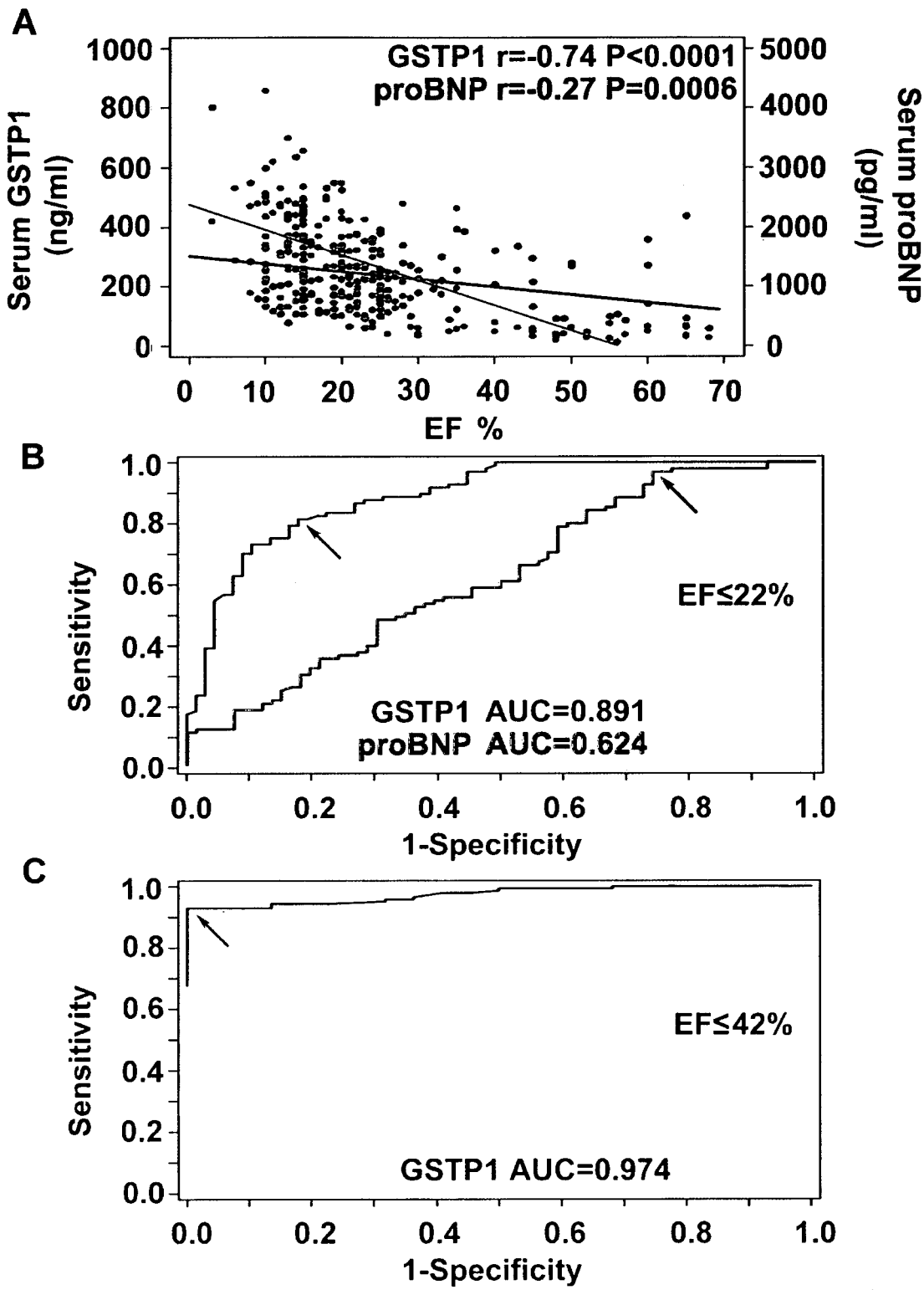

FIG. 8 shows serum GSTP1 and proBNP correlation to cardiac function. (A) Correlation of serum GSTP1 and proBNP concentrations to cardiac ejection fraction (EF) in study subjects. The analysis indicates a higher significant negative correlation of EF with serum GSTP1 (r=−0.74; P<0.0001) as compared to serum proBNP concentration (r=−0.27; P=0.0006). (B) ROC curve analysis indicates at the optimal cut-off level of ≥226 ng/ml (black line; AUC=0.891, P<0.0001) a sensitivity of 81% and a specificity of 82% for serum GSTP1 and at the optimal cut-off level of ≥527 pg/ml (red line; AUC=0.624, P=0.0039) a sensitivity of 97% and a specificity of 26% for serum proBNP to identify EF≤22%. (C) ROC curve analysis indicates at the optimal cut-off level of ≥76 ng/ml (AUC=0.974, P=0.0008) a sensitivity of 93% and a specificity of 100% for serum GSTP1 to identify EF≤42%.

Figure 9:
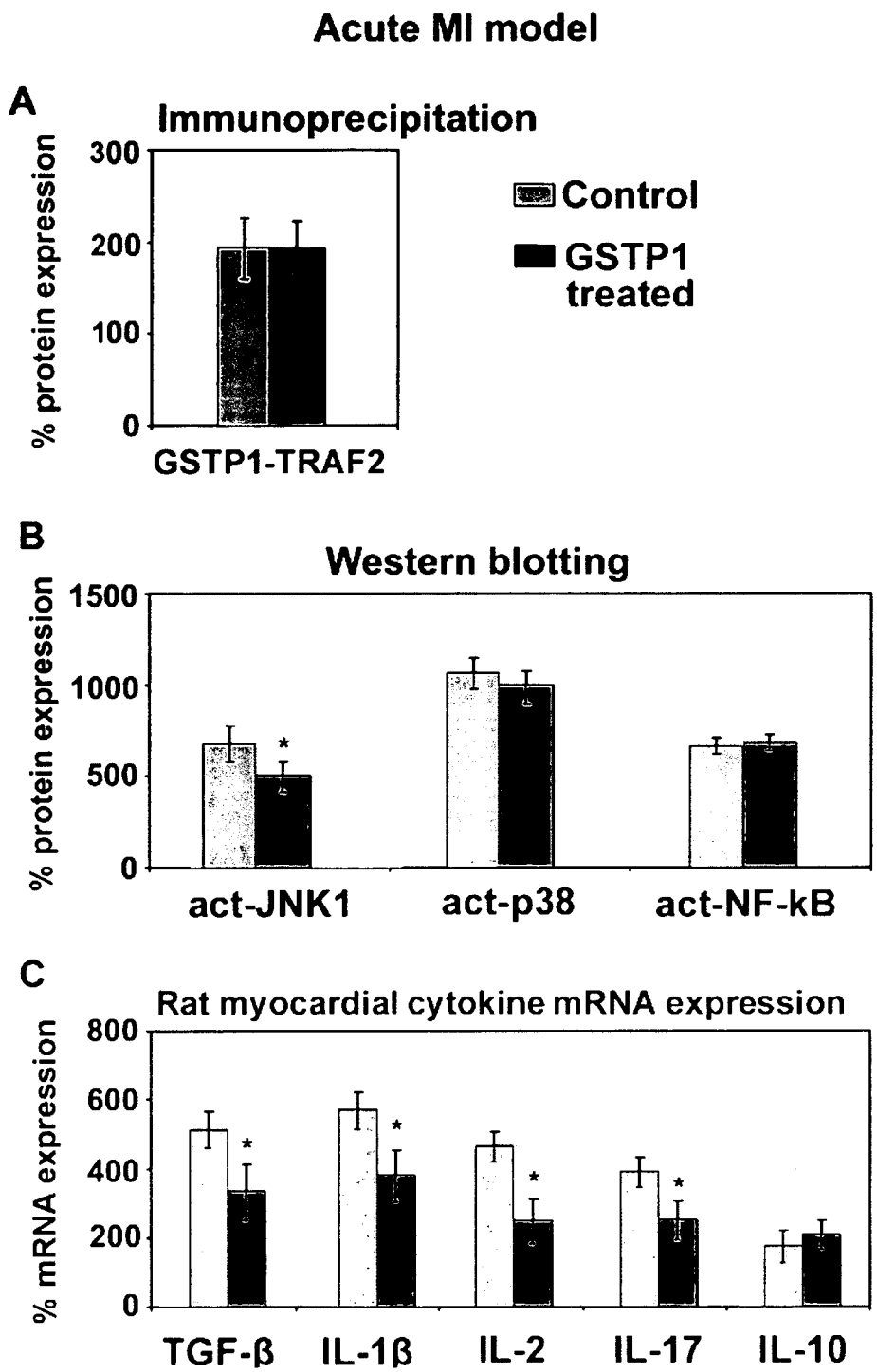

FIG. 9 shows that GSTP1 inhibits the inflammatory cytokines in a rat acute MI model. (A) Immunoprecipitation with Western blotting revealed no differences in GSTP1-TRAF2 complex formation between GSTP1-treated and control animals; (B) GSTP1 decreased activated JNK1 protein expression levels as analyzed by Western blotting; (C) GSTP1 inhibits the myocardial tissue mRNA expression of several inflammatory cytokines. *; p<0.01.

Figure 10:
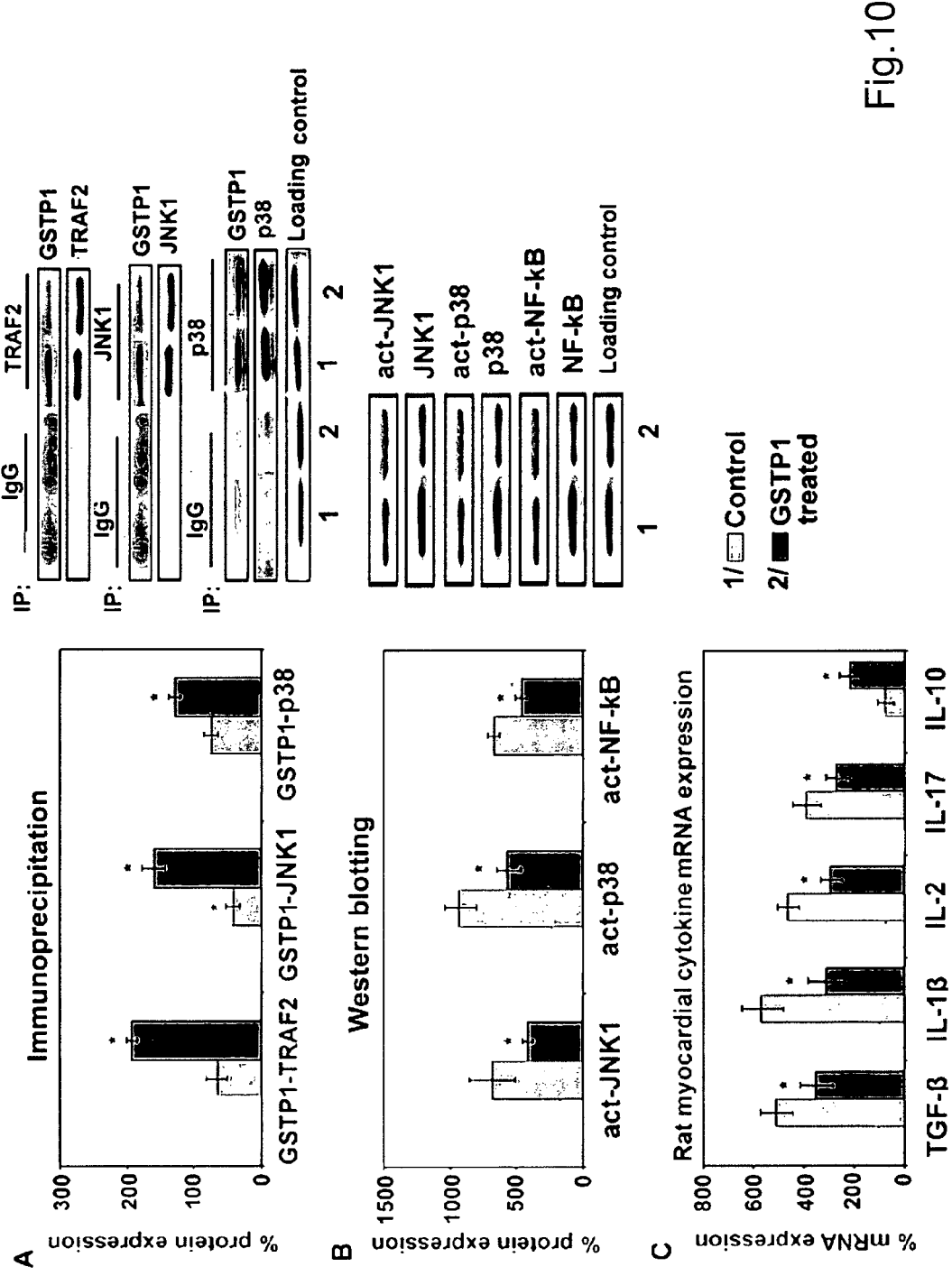

FIG. 10 shows that GSTP1 ameliorates inflammation in the rat failing heart. (A) GSTP1-treated animals had significantly higher levels of complex formation between GSTP1-TRAF2, GSTP1-JNK1 and GSTP1-p38, as shown by immunoprecipitation and Western blot analyses; (B) the protein expression of activated JNK1, p38 and NF-κB is significantly lower in GSTP1-treated animals as compared to controls as shown by Western blot analyses; (C) GSTP1 inhibits the mRNA expression of inflammatory cytokines TGF-B, IL-1B, IL-2 and IL-17; and increases the mRNA expression of anti-inflammatory cytokine IL-10 in failing myocardium as compared to controls. *; p<0.001.

Figure 11:
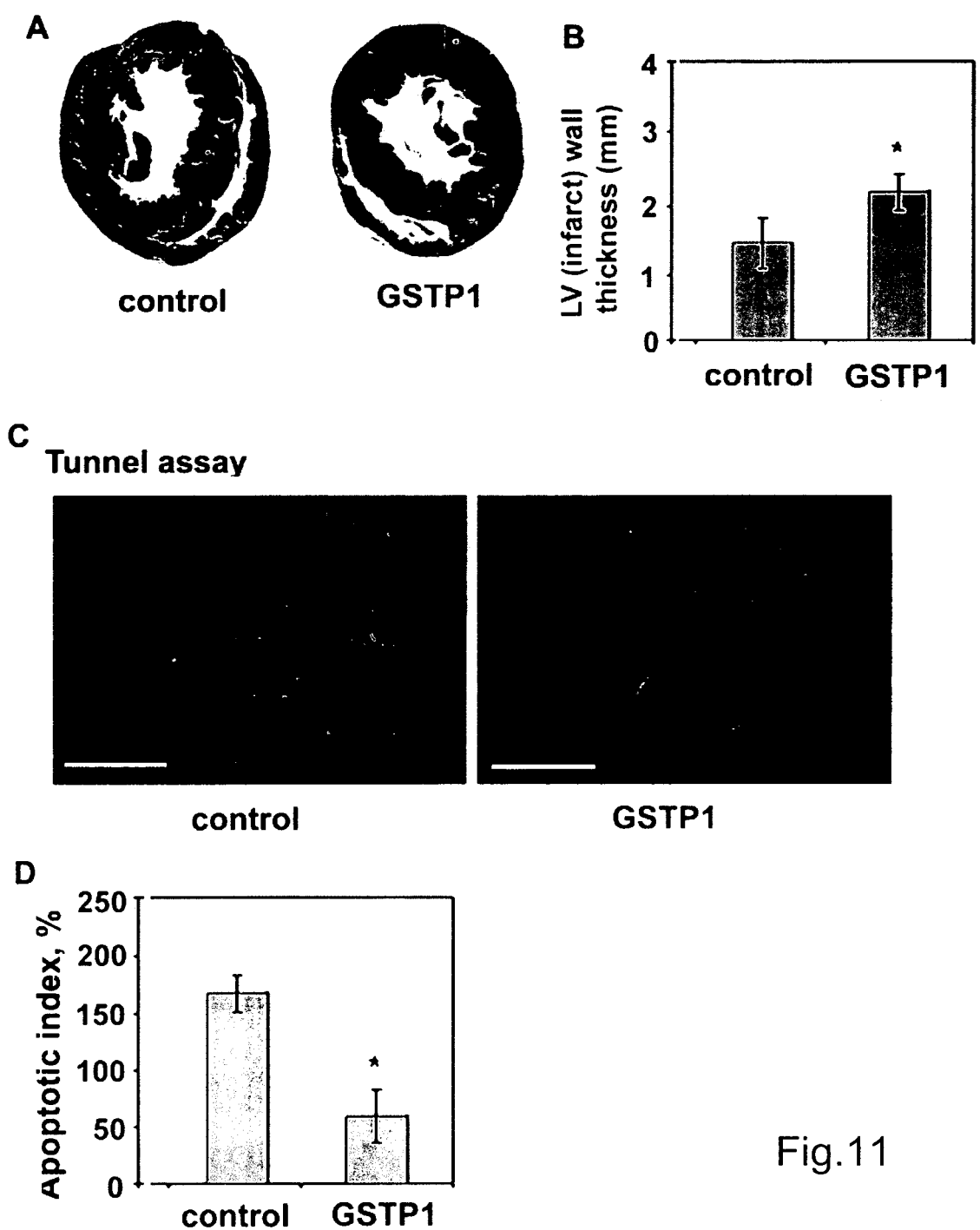

FIG. 11 shows that GSTP1 attenuates myocardial remodeling in a rat ischemia-induced model of heart failure. (A) Goldner trichrome collagen staining reveals significantly lower tissue remodeling in the heart of GSTP1-treated animals as compared to controls; (B) left ventricular (infarct) wall thickness is significantly larger in GSTP1-treated rats compared to controls; (C) representative Tunnel assay images of rat hearts treated with GSTP1 or a control vehicle. Bar=25 μm; (D) GSTP1-treated rats had a significantly lower apoptotic index as compared to controls. *; p<0.01.

Figure 12:
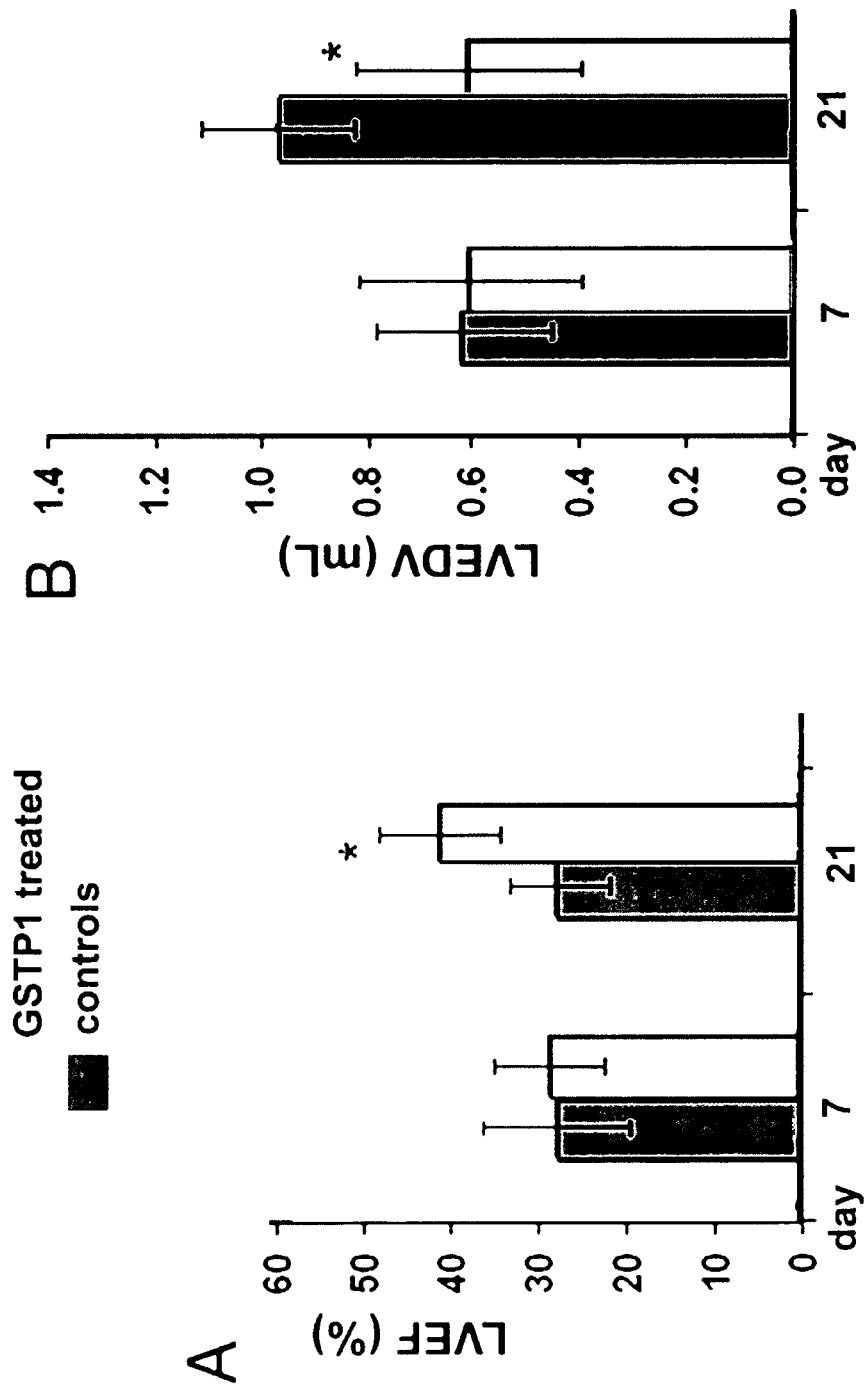

FIG. 12 shows that GSTP1 improves the left ventricular function in a rat model of ischemia-induced heart failure. (A) GSTP1-treated rats had significantly higher left ventricular ejection fraction at 21 days post-myocardial infarct; (B) the left ventricular end diastolic volume is significantly greater in controls as compared to GSTP1-treated animals. *; p<0.05.

EXAMPLES

1.: GSTP1 Ameliorates Inflammation in Cardiomyopathy (CMP) and Ischemic Heart Disease (IHD)
Patients and Tissue Sampling This study was approved by the Ethics Committee of the Medical University of Vienna. Cardiac tissue samples of 70 CMP patients who gave informed consent to be enrolled (idiopathic dilated cardiomyopathy (DCM), n=35; ischemic cardiomyopathy (ICM), n=35) were used for the initial array analyses. Then, a total of 100 CMP patients (DCM, n=50; ICM, n=50) were included between January 2004 and July 2008. Table 1 summarizes the demographic, most important clinical and hemodynamic characteristics and the treatment of patients. All patients had optimized heart failure treatment and were scheduled for cardiac transplantation according to the American Heart Association criteria. All patients underwent echocardiography, coronary artery angiography, right-heart catheterization and magnetic resonance imaging for evaluation of ventricular function, myocardial viability and standard hemodynamic parameters by independent cardiologists. The case history, clinical test results, and treatment were documented and coded and blinded to the investigators of cardiac biopsies. The control group consisted of 20 heart donors with no history of cardiac disease whose hearts could not be trans-planted due to quality reasons.

TABLE 1 demographic data, hemodynamic parameters and medication of study patients.

|  | ICM | DCM | P |
| --- | --- | --- | --- |
| Male, % | 50 | 48 | 0.4300 |
| Age (years) | 58 ± 6 | 55 ± 7 | 0.1521 |
| BMI (kg/m$^2$) | 26 ± 3 | 25 ± 4 | 0.6688 |
| BSA (m$^2$) | 1.9 ± 0.2 | 1.9 ± 0.2 | 0.5883 |
| PAP (mmHg) | 30 ± 10 | 32 ± 8 | 0.2817 |
| PCWP (mmHg) | 21 ± 9 | 22 ± 7 | 0.5264 |
| PVR (wood units) | 2.5 ± 1.2 | 2.6 ± 1.7 | 0.8185 |
| LVEF (%) | 19 ± 6 | 18 ± 6 | 0.3755 |
| Cardiac output (L/min) | 4.0 ± 0.8 | 4.4 ± 1.5 | 0.1647 |
| Cardiac index (L/min/m$^2$) | 2.1 ± 0.4 | 2.3 ± 0.8 | 0.1952 |
| ACE inhibitors (yes/no) | 23/4 | 24/11 | 0.1299 |
| Angiotensin II receptor antagonists, % | 21 | 31 | 0.2494 |
| Beta blocker, % | 96 | 83 | 0.0973 |
| Prostaglandin E2, % | 22 | 20 | 0.8312 |
| Amiodarone, % | 26 | 29 | 0.8169 |
| Levosimendan, % | 19 | 20 | 0.6959 |

ACE, angiotensin converting enzyme;
BMI, body mass index;
BSA, body surface area;
DCM, dilated cardiomyopathy;
ICM, ischemic cardiomyopathy;
LVEF, left ventricular ejection fraction;
PAP, pulmonary artery pressure;
PCWP, pulmonary capillary wedge pressure;
PVR, pulmonary vascular resistance.

cDNA array

Poly(A+)-RNA was isolated with the Oligotex-dT kit (Quiagen, Valencia Calif.) and first-strand cDNA synthesis was performed with avian myeloblastosis virus reverse transcriptase (Promega, Madison, Wis.) on 2 μg poly(A+) RNA. The RNA strand within the DNA-RNA duplex was degraded and products were purified on a Sephadex G-50 spun-column (Pharmacia, Uppsala, Sweden). For reverse-strand priming, first-strand cDNA was used to generate [α-32P]dCTP-labeled second-strand cDNA for the cDNA arrays (GEArray Q Human Apoptosis Gene Array, SuperArray Bioscience, Frederick, Md.) as described (Schäfer et al., Circulation 108 (2003), 1585-1591). Pooled cDNA hybridization signals were quantified using ImageQuant software (Molecular Dynamics, Sunnyvale, Calif.).

Cardiac Tissue Protein Array

The protein array was performed on antibody Microarray 500 (Clontech, Mountain View, Calif.; 507 proteins) as described (Aharinejad et al., Circulation 120 (2009a), 11 Suppl:S198-205). The proteins in each sample were labeled with 2 different fluorescent dyes and incubated on microarray antibody-coated slides. The protein fluorescent signals of both slides were detected by the GenePix 4000B scanner (Molecular Dynamics, Sunnyvale, Calif.). The quantification of the signal was performed by calculating an internally normalized ratio (INR), yielding the abundance of an antigen in CMP sample relative to that in control samples by using the automated Microarray Analysis Workbook (http://bioinfo.clontech.com). Proteins with INR values outside the threshold interval were considered differentially expressed.

mRNA Isolation and Quantitative Real-Time RT-PCR

Total RNA was isolated from myocardial biopsies using TRIzol (Invitrogen, Carlsbad, Calif.). The tissue was homogenized in a MagNA Lyser system (Roche, Mannheim, Germany) using MagNA Lyser Green Beads for 20-30 seconds at 6000 rpm. Homogenized samples were then mixed with 200 µL chloroform, incubated 2-3 minutes at room temperature and centrifuged at 12000 g for 15 minutes at 4° C. RNA was collected and cDNA was synthesized using 2 µg total RNA and the M-MuLV-RT kit (Fermentas, St. Leon-Rot, Germany). Real-time RT-PCR was performed on a LightCycler instrument (Roche) as described (Aharinejad et al., Am J. Transplant. 5 (2005), 2185-2192). The primer sequences were sense/antisense: GSTP1: 5'-GGCAACTGAAGC-CTTTTGAG-3'/5'-TCATGGATCAGCAGCAAGTC-3'; TRAF2: 5'-GCAGAAGGTCTTGGAGATGG-3'/5'-GGTG-GAGCAGCATTAAGGTC-3'; and β2-microglobulin: 5'-GATGAGTATGCCTGCCGTGTG-3'/5'-CAATC-CAAATGCGGCATCT-3'. mRNA expression units were determined after normalization to expression of the housekeeping gene β2-microglobulin as described previously (Aharinejad et al., 2009a and 2005; Pfaffl, Nucleic Acids Res. 29 (2001):e45) and plotted for CMP patients as percentage relative to those in controls. Measurements were performed three times. The average value of the three PCR measurements in each sample was used for data analysis.

Co-immunoprecipitation and Western Blotting

Human cardiac tissue was lysed in the lysis buffer containing 20 mM Tris (pH 7.5), 135 mM NaCl, 2 mM ethylenediaminetetraacetic acid (EDTA), 2 mM dithiothreitol (DTT), 25 mM β-glycerophosphate, 2 mM sodium pyrophosphate, 10% glycerol, 1% Triton X-100, 1 mM sodium orthovanadate, 10 mM NaF and 1 mM phenylmethylsulfonyl fluoride (PMSF) supplemented with complete protease inhibitor cocktail (Roche Applied Science, Indianapolis, Ind., USA) at 4 C as described (Aharinejad et al., 2005). Lysates were centrifuged (15 000 g) at 4 C for 15 min. For identify GSTP1-TRAF2 complexes formation proteins (500 µg) were immunoprecipitated with TRAF2 antibody (0.5 µg, BD Pharmingen, San Diego, Calif.). The precleared Protein A/G PLUS-agarose beads (Santa Cruz Biotechnology) were incubated with immunocomplexes for another 2 h and washed four times with the lysis buffer. The immunoprecipitates were further subjected on SDS-PAGE and presided with Western blotting analysis using anti-GSTP1 monoclonal anti-body (Bethyl, Montgomery, Tex.).

Protein lysates (50 µg/lane) were separated by SDS-PAGE (10%) prior to electrophoretic transfer onto a Nitrocellulose membrane (Bio-Rad, Hercules, Calif.) as described (Aharinejad et al., 2005). The blots were incubated with primary human monoclonal anti-GSTP1 antibody (Bethyl, Montgomery, Tex.), human monoclonal anti-TRAF2 (BD Pharmingen, San Diego, Calif.), human polyclonal phospho-p38 (Promega, Madison, Wis.), human polyclonal phosphor-JNK (Santa Cruz Biotechnology, Santa Cruz, Calif.), human polyclonal anti-JNK (Santa Cruz Biotechnology, Santa Cruz, Calif.), human polyclonal anti-p38 (Santa Cruz Biotechnology, Santa Cruz, Calif.), prior to incubation with horseradish peroxidase-conjugated secondary antibodies (Amersham Biosciences, Piscataway, N.J.). Protein loading was assessed by Ponceau S staining and immunodetection was performed by chemiluminescence (Supersignal-West-Pico, Pierce, Rockford, Bands were quantified by ImageQuant software and specific protein signals were normalized to loading controls and expressed as arbitrary units. The average value of three measurements in each sample was used for data analysis.

Cardiac Tissue Culture Experiments

Freshly isolated myocardium of control, DCM or ICM patients (2 to 3 $mm^3$) were incubate (100 pieces per 6-well plate) in DMEM containing 10% fetal calf serum (Gibco, Carlsbad, Calif.), 50 U/ml penicillin and 250 µg/ml streptomycin (pH 7.2) at 37° C. in a fully humidified air atmosphere containing 5% $CO_2$ as described (Schafer et al., 2003). After 6 hours, wells were treated with recombinant GSTP1 (2.5, 5 or 10 µg/ml; Assay Design, Ann Arbor, Mich.) and/or TNF-α (50 ng/ml; eBioscience, San Diego, Calif.) (Wu et al., 2006). Following incubation for 24 hours the medium was changed and cardiac tissue culture lysates were analysed. Experiments were performed in triplicate.

Statistical Analysis

Clinical parameters, patients characteristics, mRNA expression levels of GSTP1 and TRAF2, and protein expression levels of GSTP1, TRAF2, active p38, and active JNK were compared between groups by $x^2$ test and one-way analysis of variance (one-way ANOVA; Tukey's test) according to the scale of the variable (continuous or categorical). All statistical analyses were performed using SAS system for Windows, version 9.1.3 and the Enterprise Guide, version 4.1 (SAS Institute, Inc., Cary, N.C.). Statistical significance was set at P<0.05. Results are expressed as mean±standard deviation (SD).

Results

GSTP1 and TRAF2 are Overexpressed in Failing Myocardium

The screening tissue profiling arrays identified higher cardiac GSTP1 and TRAF2 gene as well as protein expression levels in randomly selected patients with both DCM and ICM compared to the control individuals (FIGS. 1A, 1B). To verify the results obtained in screening arrays, the myocardial expression of GSTP1 and TRAF2 was then prospectively examined by real time RT-PCR and Western blotting in the study cohort. These analyses indicated significantly elevated myocardial mRNA expression levels in DCM and ICM for both GSTP1 (P<0.0001) and TRAF2 (P<0.0001) as compared to controls (FIG. 1C). Likewise, myocardial protein expression levels were elevated in DCM and ICM for GSTP1 (P<0.0001, P=0.0019) and TRAF2 (P<0.0001, P=0.005) as compared to controls. (FIG. 1D). No significant differences were found in GSTP1 mRNA and protein expression when DCM and ICM were compared; although TRAF2 mRNA (P=0.001) and protein (P≤0.0001) expression levels were significantly higher in DCM as compared to ICM (FIGS. 1C, 1D).

GSTP1-TRAF2 Interaction in JNK/p38 Activation

Since GSTP1 is physically associated with TRAF2 and forms intracellular complexes in tumor cells, it was determined whether this pathway is active in the failing myocardium. The present analyses in cardiac tissue cultures showed that GSTP1 associates with TRAF2 in ICM and control cardiac tissue, while this association was significantly less (P<0.0001) detectable in DCM (FIG. 2A). As TRAF2 reportedly activates two major MAP Kinases, JNK and p38 known to mediate inflammation in failing myocardium, the myocardial expression of active p38 and JNK protein in the study patients was examined. The results show that in both DCM and ICM cardiac protein expression of active JNK as well as p38 (P<0.0001) is significantly upregulated as compared to controls. Moreover, DCM patients revealed a significantly higher cardiac JNK and p38 protein expression (P<0.0001) as compared to ICM (FIG. 2B). These results show that GSTP1-TRAF2 association is differentially regulated in DCM and ICM and that this may affect MAPKs activation.

GSTP1 Modulates Cardiac TRAF2-Mediated JNK/p38 Activation

To determine whether GSTP1 modulates TRAF2-mediated JNK and p38 activation, cardiac tissue cultures from the failing hearts and controls were treated with recombinant GSTP1 at three different concentrations. The result show that in GSTP1-treated tissue cultures obtained from DCM, ICM and controls, protein expressions of TRAF2 was significantly reduced compared to untreated ones. Similarly, following GSTP1 treatment, active JNK and p38 expression declined in DCM, ICM and control cardiac tissue compared to untreated group. The comparison of the applied GSTP1 concentrations with regard to TRAF2, JNK and p38 reduction show that in DCM and ICM but not controls the differences between 2.5 µg/mL and 5 µg/mL as well as 10 µg/mL were significant (FIGS. 3A, 3B).

To test whether exogenously supplemented GSTP1 affects GSTP1-TRAF2 complex formation, GSTP1-treated cardiac tissue lysates were immunoprecipitated with TRAF2 antibody and immunopellets were subjected to Western blotting. The results show that in GSTP1-treated cardiac tissue cultures association between GSTP1 and TRAF2 was dose and disease-independent and significantly higher (P=0.07 for 5 µg/mL GSTP1 concentration) as compared to untreated samples (FIG. 3C).

These results show that in cardiac tissue cultures GSTP1 affects TRAF2 protein expression and acts as a negative regulator of JNK1 and p38 activation through GSTP1-TRAF2 complex formation.

TNF-α Abrogates the Sensitivity of TRAF2/JNK/p38 Cascade to GSTP1 in DCM

To determine whether GSTP1 interacts with reported TNF-α-induced JNK and p38 activation in failing myocardium cardiac tissue cultures isolated from DCM, ICM and controls were treated with recombinant TNF-α followed by GSTP1 at 5 µg/ml. These experiments demonstrate that TNF-α-activated JNK (P=0.08) and p38 (P=0.75) cascade as well as TRAF2 (P=0.18) protein expression are not affected by recombinant GSTP1 in DCM cardiac tissue cultures. However, in cultures isolated from ICM and controls JNK (P<0.001; P<0.002), p38 (P<0.0002; P<0.0001) and TRAF2 (P<0.001; P=0.003) protein expressions are markedly reduced in response to GSTP1 stimulation (FIG. 4A). To understand the divergent results obtained for DCM versus ICM group, the cardiac tissue lysates treated with TNF-α and GSTP1 were immunoprecipitated and the immunopellets subjected to Western blotting. These analyses show failure of GSTP1 to associate with TRAF2 following TNF-α stimulation in DCM cardiac tissue (FIG. 4B). This effect, however, was not present in ICM and control cardiac tissue (FIG. 4C). These data show the failure of TNF-α-mediated TRAF2 binding to GSTP1 in DCM cardiac tissue cultures at 5 µg/ml GSTP1.

GSTP1 Rescues TRAF2-Mediated JNK1/p38 Downregulation Following TNF-α Treatment at Higher Concentrations Keeping in mind that TRAF2 cardiac protein expression in DCM was approximately two times higher as compared to ICM and controls and considering the results described above, we tested the effect of higher GSTP1 concentration following TNF-α treatment. The results demonstrate that DCM cardiac tissue cultures treated with GSTP1 at 10 µg/mL and TNF-α at 50 ng/mL express markedly reduced JNK and p38 activation as well as reduced TRAF2 protein expression (P<0.0001; FIGS. 5A, 5B). Importantly, the immunoprecipitates of DCM cardiac tissue lysates demonstrate significant (P≤0.035) increase of GSTP1-TRAF2 association at 10 µg/ml as compared to 5 mg/ml GSTP1.

These data show that higher GSTP1 concentrations inhibit TNF-α-induced JNK and p38 activation in DCM through GSTP1-TRAF2 complex forming and also affect TRAF2 expression.

In the present example GSTP1 and TRAF2 were identified as novel mediators of CMP. Interaction between GSTP1 and TRAF2 has been previously identified in malignancies (Wu et al. 2006), however, connection to CMP has not been suggested before. Interestingly, the ability of GSTP1 to associate with TRAF2 differed between DCM and ICM in a TNF-α dependent manner. Although the devastating pro-inflammatory role of TNF-α signalling in CMP is well established, clinical trials have paradoxically indicated a more complicated role for TNF-α in CMP. Targeting specific pathways related to TNF-α signalling might therefore provide a more selective approach in CMP treatment. TRAF2 is a central regulator of TNF-α signalling that mediates MAPK activation. At the same time, GSTP1 can abrogate MAPK activation through association with TRAF2 and consequently suppress TNF-α signalling. The present data show significant elevation of active JNK and p38 in DCM myocardium compared to ICM and controls.

Importantly, it was demonstrated that replenishing intracellular stores of GSTP1 with recombinant GSTP1 protein effectively suppresses systemic and localized inflammatory responses through inhibition of MAPK signalling. Intriguingly, in contrast to the findings observed in native DCM myocardium in this study, recombinant GSTP1 induced the inhibition of JNK and p38 activities as well as decreasing total TRAF2 protein expression in cardiac tissue cultures. This effect was accompanied by a considerable increase in GSTP1-TRAF2 association in all GSTP1 treated cardiac cell cultures. Moreover, maximal effects of GSTP1 attenuation on the TRAF2-JNK/p38 system were observed at 5 µg/ml and were not affected by further concentration increases. These results contradict those obtained with cardiac tissue. However, after GSTP1 treatment, expression levels of active JNK/p38 and TRAF2 were highest in cultures from DCM patients. Since no differences in GSTP1-TRAF2 complex formation upon GSTP1 incubation were observed in DCM compared to ICM and control cardiac tissue cultures, additional factors could contribute to intracellular regulation of GSTP1-TRAF2 association in CMP. The discrepancy between data obtained by analysis of myocardial samples and in vitro experiments could be explained by the presence of a soluble, circulating factor normally present in native myocardium but not in cardiac tissue cultures. Since TNF-α is highly elevated in the serum of CMP patients and has been implicated in the underlying pathology, cardiac tissue cultures were pre-incubated prior to recombinant GSTP1 administration in order to introduce the effects of TNF-α in the in vitro model. Remarkably, incubation of TNF-α stimulated cardiac tissue cultures with 5 µg/ml GSTP1 did not affect GSTP1-TRAF2 association in ICM cardiac cultures whereas in DCM cardiac cultures, GSTP1-TRAF2 complex formation was completely abrogated. Moreover, unchanged high expression of active JNK/p38 as well as TRAF2 was observed exclusively in DCM cardiac tissue cultures. These results are in agreement with those obtained by analysis of myocardial biopsies and fully support that impaired GSTP1-TRAF2 interaction in DCM patients resulted in increased activity of MAPKs.

These data show, that further increases of GSTP1 concentration restore GSTP1-TRAF2 association and inhibit JNK1 and p38 activity in DCM cardiac tissue cultures upon TNF-α stimulation. These results show that the TNF-α induced attenuation of GSTP1-TRAF2 binding which is solely associated with DCM pathology, can be abrogated by higher concentrations of GSTP1. Moreover, it was demonstrated that in ICM cardiac tissue cultures both JNK1 and p38 activity is inhibited by recombinant GSTP1 in a dose and TNF-α independent manner. These results show that GSTP1 action in ICM may occur though a TRAF2-independent manner.

In conclusion, these results show the novel function of GSTP1 in modulating TNF-α/TRAF2 elicited JNK1/p38 activation in DCM. In addition, GSTP1-TRAF2 association is guarded by TNF-α stimulation in DCM but not ICM or control myocardium in a GSTP1 concentration dependent manner. These findings show (see also: post published abstract Aharinejad et al., Circulation 120 (November 2009), S905; enhancement of cardiovascular sensitivity to cyclophosphamide: Haberzettl et al., Circulation 120 (November 2009), S718) the functionality of the present invention as a reliable, advanced therapeutic strategy targeting the anti-inflammatory acting of GSTP1.

2.: Serum GSTP1 is a Sensitive Marker of CMP

Patients and Methods

Patients

This study was approved by the Ethics Committee of the Medical University of Vienna. Serum samples of CMP patients (EF≤35%; n=40) and healthy volunteers (EF≤65%; n=40) were used for the initial array analyses. Then, a total of 161 patients who gave informed consent to be enrolled were prospectively included. The study cohort comprised 141 end-stage CMP patients scheduled for cardiac transplantation and 20 patients with preserved EF undergoing conventional isolated aortic or mitral valve surgery. All patients underwent echocardiography, coronary artery angiography, and right-heart catheterization for evaluation of ventricular function and standard hemodynamic parameters by two independent cardiologists. The case history, clinical test results, and treatment were documented, coded and blinded to the investigators of serum samples.

The study patients were subdivided in groups based on their left ventricular EF assessed by echocardiography as follows: EF>52%; EF 52-43%; EF 42-33%, EF 32-23% and EF≤22% as described (Lee et al., Circulation 119 (2009) 3070-3077). The control group (n=20) consisted of 10 males and 10 females, aged 30-61 years (51.8±3.2 years).

Serum and Cardiac Tissue Collection

Peripheral venous blood samples were collected at CMP diagnosis or shortly before transplant (Aharinejad et al., Am. J. Transplant. 9 (2009b), 149-159). Serum samples were coded and stored in liquid nitrogen until analysis. Multiple myocardial biopsies were obtained from the anterior left ventricular wall (LV) of the explanted hearts of transplant patients (EF≤35%; n=40) and from 20 donor hearts that could not be transplanted for quality reasons (EF≥65%, mean age 45±10, 12 males, 8 females), coded and snap frozen in liquid nitrogen.

Serum and Cardiac Tissue Protein Arrays

For protein array randomly selected serum samples were obtained from end-stage CMP patients shortly before transplant and from healthy volunteers and pooled for each group. For cardiac tissue protein array the tissue lysates (Abraham et al., Circ. Res. 87 (2000), 644-647) from LV myocardial biopsies of explanted hearts in transplant patients (n=40) and donor control hearts (n=20) were used. The protein array was performed on antibody Microarray 500 (Clontech, Mountain View, Calif.; 507 proteins), according to the manufacturer's protocol. The proteins in each sample were labeled with 2 different fluorescent dyes (Cy3 and Cy5) and incubated on microarray antibody-coated slides. The protein fluorescent signals of both slides were detected by the GenePix 4000B scanner (Molecular Dynamics, Sunnyvale, Calif.). The quantification of the signal was performed by calculating an internally normalized ratio (INR) using the automated Microarray Analysis Workbook (http://bioinfo.clontech.com).

GSTP1 and Pro BNP Assays

Enzyme linked immunosorbent assay (ELISA) for GSTP1 (HEPKIT™-Pi, Biotrin International Ltd., Dublin, Ireland) was performed according to the manufacturer's protocol. The substrate reaction was quantified spectrophotometrically by using a 96-well automated microplate reader (Anthos, Salzburg, Austria) at 450 nm. N-terminal proBNP was measured in undiluted serum automatically by a chemiluminescent noncompetitive ELISA (Roche Diagnostics, Indianapolis, Ind.) on a Roche Elecsys 2010 analyzer.

mRNA Isolation and Quantitative Real-time RT-PCR

Total RNA was isolated from LV biopsies using TRIzol (Invitrogen, Carlsbad, Calif.) with a MagNA Lyser system (Roche, Mannheim, Germany). Real-time RT-PCR was performed on a LightCycler instrument (Roche) as described (Aharinejad et al., 2009b, Abraham et al, 2000). The primer sequences were sense/antisense: GSTP1: 5'-CCAAAGGTG-GTGAGCTTCAT-3'/5'-TCTACCCAGCATGGAGGAAC-3'; and β2-microglobulin: 5'-GATGAGTATGCCTGCCGT-GTG-3'/5'-CAATCCAAATGCGGCATCT-3'. mRNA expression levels of GSTP1 was normalized to the β2-microglobulin signal as a housekeeping gene (Aharinejad et al., 2009b, Abraham et al, 2000). The average value of three PCR measurements in each sample was used for data analysis.

Western Blotting Analysis

Tissue lysates were prepared (Aharinejad et al., 2009b) and GSTP1 expression was analyzed by Western blotting using primary human monoclonal anti-GSTP1 antibody (Bethyl, Montgomery, Tex.). Protein bands were quantified by ImageQuant software and specific protein signals were normalized to loading controls. The average value of three measurements in each sample was used for data analysis.

Statistical Analysis

GSTP1 and proBNP serum concentrations were compared between patient groups by analysis of variance (one-way ANOVA; Tukey's test). To investigate the relationship between GSTP1 and proBNP, as well as the relationship of GSTP1 to age, PAP, PCWP, PVR, cardiac index and creatinine, Spearman's rank correlation coefficients (rS) were computed. Univariate logistic regression was used to describe the utility of GSTP1 and proBNP as predictors of EF. The corresponding receiver operating characteristic curve (ROC) analyses were used to find optimal cut-off levels. Sensitivity and specificity of GSTP1 and proBNP cut-offs were calculated by table analysis. All statistical analyses were performed using SAS system for Windows, version 9.1.3 and the Enterprise Guide, version 4.1 (SAS Institute, Inc., Cary, N.C.). Statistical significance was set at P<0.05. Results are expressed as mean±standard deviation.

Results

GSTP1 is Associated with CMP

The demographic data, clinical characteristics and the most CMP-relevant medication of the study patients are shown in Table 2.

TABLE 2

Demographic data, clinical characteristics and the most CMP-relevant medication of the study patients.

| Characteristic | Value |
|---|---|
| Age (years) | 53 ± 13 |
| Male/Female | 119/42 (74%/26%) |
| Diabetes mellitus | 34 (21%) |
| IDDM | 22 (14%) |
| NIDDM | 12 (7%) |
| NYHA Functional Classification | |
| II | 25 (15%) |
| III | 94 (59%) |
| IV | 42 (26%) |
| Diagnosis | |
| Valvular Disease | 20 (12%) |
| ICM | 43 (27%) |
| DCM | 86 (53%) |
| Others | 12 (8%) |
| Hemodynamic parameters | |
| EF (%) | 24 ± 14 |
| PAP (mmHg) | 31 ± 9 |
| PCWP (mmHg) | 21 ± 8 |
| PVR (Wood units) | 2.58 ± 1.41 |
| Cardiac Index (l/min/m$^2$) | 2.20 ± 0.64 |
| Laboratory findings | |
| Creatinine (mg/dl) | 1.32 ± 0.44 |
| GSTP1 (ng/ml) | 271 ± 173 |
| proBNP (pg/ml) | 1200 ± 630 |
| Medication | |
| ACE blocker | 111 (69%) |
| Angiotensin II receptor antagonists | 39 (24%) |
| Beta blocker | 131 (81%) |
| Levosimendan (SIMDAX) | 21 (13%) |

DCM = dilated cardiomyopathy;
EF = left ventricular ejection fraction;
ICM = ischemic cardiomyopathy;
IDDM = insulin-dependent diabetes mellitus;
NIDDM = non-insulin-dependent diabetes mellitus;
NYHA = New York Heart association;
PAP = pulmonary artery pressure;
PCWP = pulmonary capillary wedge pressure;
PVR = pulmonary vascular resistance.

In the targeted protein array screen of pooled serum samples in selected CMP patients GSTP1 was identified as a novel protein to be associated with CMP. FIG. 6A shows the array images of GSTP1 and indicates that its serum protein levels are increased in CMP patients as compared to healthy volunteers. Following these screening analyses, serum GSTP1 concentration was determined in the same patient cohort selected for screening analyses by GSTP1-specific ELISA. These results show that serum GSTP1 concentrations were significantly upregulated in end-stage HF patients as compared to the control samples (FIG. 6B, P≤0.001).

To learn about the myocardial GSTP1 protein levels, a tissue protein profiling was initiated using the LV myocardial samples of the same end-stage HF patients analysed by serum arrays and used LV myocardial biopsies of donated hearts as controls. The results of tissue profiling indicate elevated GSTP1 expression levels in myocardium of end-stage HF patients as compared to controls (FIG. 6C). To validate these findings, Western blotting analyses were performed on cardiac tissues and found significantly upregulated GSTP1 protein expression levels in patients with end-stage HF as compared to controls (P<0.001; FIG. 6D).

Association of GSTP1 and proBNP with EF

To understand the association of GSTP1 with CMP, its serum levels were analyzed in all study patients and plotted these results in relation to the patient's EF. By selecting this type of analysis that enables differentiation between preserved and reduced EF, significantly higher serum GSTP1 concentrations were found in patients with EF≤22% as compared to all other EF groups (FIG. 7A; P<0.0001). In addition, CMP patients with an EF between 23-32% and EF 33-42% had significantly higher GSTP1 serum concentrations as compared to those with an EF between 43-52% or >52% (FIG. 7A; P<0.0001). The same type of analysis for serum proBNP revealed that in the present patient cohort only those with EF≤22% had significantly higher serum proBNP concentrations (P<0.0001) as compared to all other EF groups except for patients with an EF between 33-42% (FIG. 7B). No significant differences were observed for circulating proBNP when other EF groups were compared. In the entire population, a significant positive relationship was noted between GSTP1 and proBNP (r=0.47, P<0.0001; FIG. 7C).

Diagnostic Value of Serum GSTP1 as Compared to proBNP in CMP

To illustrate the correlation between serum GSTP1 and proBNP with EF a skater plot analysis was performed including all study patients (FIG. 8A). These analyses revealed a significant negative correlation (r=−0.74; P<0.0001) between GSTP1 and EF which was higher than the correlation between proBNP and EF (r=−0.27; P=0.0006). When entering the serum GSTP1 measurements in ROC curve analysis for the EF≤22%, which was identified to be significantly different for both GSTP1 and proBNP in univariate logistic regression analyses, at an optimal cut-off level of ≥226 ng/ml serum GSTP1 had a sensitivity of 81% and a specificity of 82% to identify EF≤22% (AUC=0.891, P<0.0001). The same type of analysis at a cut-off level of ≥527 μg/ml revealed a sensitivity of 97% and a specificity of 26% for serum proBNP to diagnose CMP patients with EF≤22% (AUC=0.624, P=0.0039)(FIG. 8B). Then the ability of GSTP1 serum levels to diagnose higher EF patient groups was analyzed, as indicated by the univariate analyses shown above (proBNP was not significantly different between patients groups with EF>22%). The ROC curve analyses indicated that GSTP1 at an optimal cut-off level of ≥76 ng/ml diagnoses CMP patients with EF≤42% with a 93% sensitivity and a 100% specificity (AUC=0.974, P=0.0008) (FIG. 8C).

Correlation of GSTP1 and proBNP with Demographic and Clinical Parameters

The associations between GSTP1 and proBNP and clinical characteristics of the study patients is illustrated in Table 3.

TABLE 3

Spearman correlation analysis between GSTP1 and proBNP and clinical variables of study patients

| | GSTP | | proBNP | |
|---|---|---|---|---|
| Covariates | $r_s$ | P | $r_s$ | P |
| GSTP1 ng/ml | | | 0.4690 | <0.0001 |
| EF | −0.7442 | <0.0001 | −0.2666 | 0.0006 |
| Age (years) | −0.1375 | 0.0241 | 0.1756 | 0.0259 |
| PCWP (mmHg) | 0.0577 | 0.5027 | −0.0451 | 0.6039 |
| PVR (Wood units) | −0.0620 | 0.4682 | −0.0594 | 0.4908 |
| Cardiac Index (l/min/m$^2$) | −0.1103 | 0.2534 | 0.1531 | 0.1153 |
| Creatinine (mg/dl) | −0.1560 | 0.0686 | −0.0649 | 0.4543 |

EF = ejection fraction;
PAP = pulmonary artery pressure;
PCWP = pulmonary capillary wedge pressure;
PVR = pulmonary vascular resistance.

For both serum GSTP1 (r=−0.137; P=0.0241) and proBNP (r=0.175; P=0.0259) only a slightly but not relevant correlation with patient age was found among the study patients. No significant correlation between serum GSTP1 concentration and pulmonary artery pressure, pulmonary capillary wedge pressure, pulmonary vascular resistance, serum creatinine level and cardiac index was observed. Likewise, no association to gender and diabetes mellitus (P≥0.408) was observed for both serum GSTP1 and proBNP.

Significant treatment gaps in the use of evidence-based management persist despite optimistic results from randomized clinical trials. The emergence of cardiac biomarkers as increasingly effectual clinical tools suggests the potential to successfully guide therapy and reduce disease burden. Innovative studies have identified a variety of novel molecular markers of diagnostic and prognostic value in CMP. ProBNP is currently accepted as a surrogate parameter in CMP monitoring, yet the clinical routine work indicates divergent results in CMP patients. The purpose of the present study was therefore to find a non-invasive and rapidly responding CMP serum marker that allows monitoring of CMP patients with both reduced and preserved EF. The targeted screening according to the present invention showed that GSTP1 is associated with end-stage CMP. Serum GSTP1 concentrations specifically diagnosed CMP with significant association to EF independently from demographical and clinical characteristics in our patient cohort. Of note, markedly higher correlation coefficients were shown for serum GSTP1 association to EF as compared to proBNP. In addition, serum GSTP1 shows better diagnostic power in CMP patients with EF≤22% as compared to proBNP. More importantly, GSTP1 diagnosed EF≤42% whereas proBNP failed.

It is well established that EF is a determinant of cardiac risk in CMP patients. The hazard ratio for all-cause mortality increased by 39% for every 10% reduction in EF below 45%. However, CMP clinical features can occur in patients with EF>45% referred to as CMP with preserved EF. Thus the present finding that GSTP1 is able to discriminate CMP patients with EF≤42% is of important diagnostic and prognostic significance. Although proBNP is an established tool for CMP diagnosis and correlates to EF the reported values regarding proBNP are quite divergent and are evidently elevated in both CMP with preserved EF and reduced EF resulting in its limited clinical use. On the other hand proBNP is recommended to be mainly used for exclusion of CMP with normal EF in patients with symptoms attributed to CMP. However, given that gender and older age are associated with higher proBNP levels (Costello-Boerrigter et al., J. Am. Coll. Cardiol. 47 (2006), 345-353), the proposed diagnostic properties of proBNP might be too unspecific to differentiate CMP with preserved EF in elderly patients.

Reportedly, proBNP can predict EF<30% with a sensitivity and specificity of 90% and 71%, respectively in a CMP population with EF<45%. Other studies reported that plasma proBNP detect EF<28% with 77% sensitivity and 69% specificity in a patients cohort with EF<50%, and it was found that proBNP can predict EF<40% with an area under the curve of 0.69. In the present study proBNP had 97% sensitivity but only 26% specificity to diagnose EF≤22% with an area under the curve of 0.62. The lower specificity of proBNP in the present study could be explained by the fact that our cut-off level was selected to identify lower EFs as compared to other studies. This criterion was selected to demonstrate utility of GSTP1 for diagnosing EF≤22%. Moreover, the present study had no exclusion criteria for EF and this could have influenced the test characteristics regarding proBNP that was previously shown to vary in CMP patients with preserved EF.

The reason for serum GSTP1 rising in CMP patients is unclear. However, evidence is accumulating that GSTP1 participates in regulation of stress signalling and protects cells against apoptosis via its non-catalytic, ligand-binding activity.

The results of the present study show that GSTP1 is a sensitive, specific, cheap and quickly measurable serum marker superior to proBNP in CMP. Importantly, GSTP1 discriminates between preserved and reduced EF with a high sensitivity and specificity and can therefore serve as a novel tool in guiding of clinical trials in CMP patients.

3.: Animal IHD and CMP Model for GSTP1 Treatment

In order to have a model that mimics both IHD and CMP in humans, the model of ligation of the anterior branch of the left coronary artery in the rat has been selected to further prove the principle of the present invention. In this model, IHD is induced following the ligation of the said coronary artery branch, and over time the animals will subsequently develop CMP. Therefore, the model is best suited to show the efficacy of the suggested invention for prevention or treatment of both IHD and CMP.

The following experiments will be performed according to the published protocol by Aharinejad et al. (Cardiovasc. Res. 79 (2008), 395-404). The investigation will conform to the Guide for the Care and Use of Laboratory Animals published by the US National Institutes of Health (NIH Publication No. 85-23, revised 1996) and will be confirmed by the Institutional Ethics Committee at the Medical University of Vienna. Prof. Dr. Seyed-hossein Aharinejad, Md., PhD will be in charge of the design and supervision of performing the study.

Male, Sprague Dawley rats (Harlan, Borchen, Germany) will be coded for experiments. Due to expected hemodynamic compromise, ventricular fibrillation, myocardial rupture and bleeding following myocardial infarction (MI), the number of surviving animals is expected to be about 60-70%. Therefore, in each group with myocardial infarction, a total of 18 animals will be included. Rats will be anesthetized with intraperitoneal injection of Ketasol (100 mg/kg body weight) and Rompun (10 mg/kg body weight), intubated tracheally using a 14-gauge catheter and ventilated with 1.5% Isofluran at 55 cycles per minute (tidal volume: 2.5 ml) before undergoing a left lateral thoracotomy. The anterior branch of the left coronary artery (LCA) will be either ligated with a 7-0 polypropylene snare (Ethicon, Somerville, N.J.) or left intact in sham procedure. At day (d) 7 post MI, left ventricular (LV) function will be assessed by echocardiography. Then, animals with comparable base-line cardiac function will be coded and assigned to groups 1-8 as shown in Table 4. To treat the expected pain following MI, animals will receive immediately after MI induction and on the first day post MI 0.6 mg/100 g body weight Piritramid (Dipidolor© in 5% glucose solution) s.c. Further, animals will receive Piritramid via their drink water for 3 days at 0.6 mg/100 g body weight (250 ml water plus 20 ml 5% glucose solution) and at days 4-7 post MI at 0.3 mg/100 g body weight.

On d7, immediately after MI induction, treatment will start in groups 1-4 as follows. Group 1 will receive daily intraperitoneal injections of Ringer's solution for two weeks (control), while groups 2-4 will receive daily injections of recombinant GSTP1 at a dose of 10, 20 and 40 mg/body weight for two weeks, respectively. On d21 the treatment will start in groups 5-8 as follows. Group 5 will receive daily intraperitoneal injections of Ringer's solution for two weeks (control), while groups 6-8 will receive daily injections of recombinant GSTP1 at a dose of 10, 20 and 40 mg/body weight for two weeks, respectively. Group 9 includes 10 animals with sham procedure. On d52 and d86, the LV function will be reassessed, and animals will be sacrificed on day 88 post MI.

TABLE 4

Groups of animals and their treatment

| Group | Treatment | Sacrifice | No. of animals | Application and dose |
|---|---|---|---|---|
| 1 | Ringer | d88 | 18 | i.p. |
| 2 | GSTP1 | d88 | 18 | i.p., 10 mg/kg bw, 2 weeks |
| 3 | GSTP1 | d88 | 18 | i.p., 20 mg/kg bw, 2 weeks |
| 4 | GSTP1 | d88 | 18 | i.p., 40 mg/kg bw, 2 weeks |
| 5 | Ringer | d88 | 18 | i.p. |
| 6 | GSTP1 | d88 | 18 | i.p., 10 mg/kg bw, 2 weeks |
| 7 | GSTP1 | d88 | 18 | i.p., 20 mg/kg bw, 2 weeks |
| 8 | GSTP1 | d88 | 18 | i.p., 40 mg/kg bw, 2 weeks |
| 9 | Sham | d88 | 10 | — |
| Total No. of animals | | | 154 | |
| 1 | Ringer | d88 | 18 | i.p. |
| 2 | GSTP1 | d88 | 18 | i.p., 10 mg/kg bw, 2 weeks |
| 3 | GSTP1 | d88 | 18 | i.p., 20 mg/kg bw, 2 weeks |
| 4 | GSTP1 | d88 | 18 | i.p., 40 mg/kg bw, 2 weeks |
| 5 | Ringer | d88 | 18 | i.p. |
| 6 | GSTP1 | d88 | 18 | i.p., 10 mg/kg bw, 2 weeks |
| 7 | GSTP1 | d88 | 18 | i.p., 20 mg/kg bw, 2 weeks |
| 8 | GSTP1 | d88 | 18 | i.p., 40 mg/kg bw, 2 weeks |
| 9 | Sham | d88 | 10 | |
| Total No. of animals | | | 154 | | bw: body weight

The following parameters will be evaluated (1-11):
1. LV ejection fraction (EF), LV end systolic volume (ESV), LV end diastolic volume (EDV) using echocardiography
2. Heart-to-body weight ratio
3. Histology and immunocytochemistry for infarct size, infarct wall thickness and fibrosis as well as angiogenesis, inflammatory proteins including p38, june kinase and interleukins (only examples are mentioned for inflammatory pathways)
4. Signaling pathways
5. Promoter binding assays
6. TUNEL-assay for apoptosis evaluation
7. Quantitative RT-PCR as well as Western Blotting, and immunoprecipitation for evaluation of GSTP1 and related to its pathways, TRAFs, TNF-α and its receptors; MMPs and their inhibitors TIMPs, VEGF-A and its receptors (only examples are mentioned here)
8. ELISA of serum GSTP1 levels and related proteins All data will be coded and stored by using Microsoft ACCESS. Analysis of variance (ANOVA; t-Test or non-parametric ANOVA) and chi2 test will be used based on dependence of the parameter to be analyzed (numeric or alphanumeric, normal distribution or not) to compare the data between the groups. The Spearmans' correlation test and logistic regression analysis will be used to assess the correlation between the evaluated parameters. SAS version 9.1.3 will be used for statistical analyses.

4.: Effect of GSTP1 Treatment on Inflammation, Cardial Morphology and Function in a Rat Model of Acute Myocardial Infarction and Ischemic-Induced Heart Failure The following experiment proves the principle, whether glutathione S-transferase P1-1 (GSTP1) treatment is beneficial in counteracting the inflammatory cascades activated following acute myocardial infarction and in the process of the resulting ischemia-induced heart failure in an accepted experimental rat model.

Materials and Methods

Animals and Myocardial Infarction Model

All experiments were approved by the Institutional Animal Care and Use Committee at the Vienna Medical University. A total number of 60 male Sprague Dawley rats (Harlan, Borchen, Germany) were coded for experiments. Due to hemodynamic compromise, ventricular fibrillation, myocardial rupture and bleeding following myocardial infarction, the number of surviving animals with comparable base-line cardiac function was 48. Rats were anaesthetized, intubated tracheally and ventilated with an oxygen/isoflurane mixture before undergoing a left lateral thoracotomy. The branch of the left coronary artery was then ligated with a 7-0 polypropylene snare (Ethicon, Somerville, N.J., USA). An intraperitoneal single dose injection of either recombinant GSTP1 (1 mg/kg dissolved in 1 ml phosphate-buffered saline (PBS); n=24) (Assay Design, Ann Arbor, Mich.) or 1 ml PBS (n=24) was applied 1 h after induction of myocardial infarction. The left ventricular (LV) function was assessed by echocardiography one day (n=48) and three weeks (n=24) after induction of myocardial infarction as described below. A total of 12 animals in each group were then sacrificed one day after treatment; and the remaining 12 animals in each group were sacrificed 3 weeks after induction of myocardial infarction (Aharinejad et al., 2008).

Echocardiography Hemodynamic Measurements

In anesthetized rats, maximal LV long-axis lengths (L) and endocardial area tracing were measured using a 15 MHz linear array scan head to calculate LV end-diastolic (LVEDV) and endsystolic (LVESV) volume and ejection fraction (LVEF=LVEDV−LVESV/LVEDV). Measurements utilized three consecutive cardiac cycles (Aharinejad et al., 2008).

Histology and Immunocytochemistry

The ventricles were cross-sectioned at the midpoint of their long axis, before they were either frozen or immersion-fixed in formalin. Paraffin-embedded specimens were used for H&E, Tunnel assay as well as Goldner trichrome collagen staining. TUNEL assays (In situ Cell Death Detection Kit) were performed according to the manufacturer's protocol (Roche Molecular Biochemicals, Basel, Switzerland) in triplicate. Slides were counterstained with 4,6-diamidino-2-phenylindole (DAPI, Molecular Probes, Eugene, Oreg.) and embedded in AF1 antifadent (Citifluor, Leicester, UK). Digital images were obtained by fluorescence microscopy (Nikon, Melville, N.Y.). Morphometry was carried out as described (Aharinejad et al., 2008).

mRNA Isolation and Quantitative Real-Time RT-PCR

Total RNA was isolated from myocardial tissues using TRIzol (Invitrogen, Carlsbad, Calif.) and MagNA Lyser system (Roche, Mannheim, Germany) as described (Aharinejad et al., 2008). Realtime RT-PCR measurements in triplicates were performed on a LightCycler instrument (Roche) as described (Aharinejad et al., 2008). The primer sequences were sense/antisense: GSTP1: 5'-GGCAACTGAAGC-CTTTTGAG-3'/5'-TCATGGATCAGCAGCAAGTC-3'; tumor necrosis factor receptor-associated factor 2 (TRAF2): 5'-GCAGAAGGTCTTGGAGATGG-3'/5'-GGTGGAG-CAGCATTAAGGTC-3'; and 132-microglobulin: 5'-GAT-GAGTATGCCTGCCGTGTG-3'/5'-CAATCCAAATGCG-GCATCT-3'. mRNA expression were calculated and plotted for treated animals as percentage relative to that in controls.

Co-immunoprecipitation and Western Blotting

Cardiac tissue lysates were prepared as described (Schafer et al., 2003). For GSTP1-TRAF2, GSTP1-JNK1 and GSTP1-p38 complex detection, proteins (500 µg) were immunoprecipitated with 0.5 µg of corresponding antibodies against TRAF2 (BD Pharmingen, San Diego, Calif.), JNK1 and p38 (Santa Cruz Biotechnology, Santa Cruz, Calif.). The immunocomplexes were incubated with A/G PLUS-agarose beads (Santa Cruz Biotechnology) and precipitated by Western blotting using GSTP1 antibody (Bethyl, Montgomery, Tex.) as described (Schafer et al., 2003). The blots were incubated with primary human monoclonal GSTP1 (Bethyl) and TRAF2 (BD Pharmingen) or polyclonal phospho-p38 (Promega, Madison, Wis.), phospho-JNK1, JNK1 and p38 (Santa Cruz Biotechnology) antibodies prior to incubation with secondary antibodies (Amersham Biosciences, Piscataway, N.J.). All experiments were performed in triplicate and expression levels were corrected for control loading protein.

Statistical Analysis

All parameter were compared between groups by $x^2$ test and one-way analysis of variance (one-way ANOVA; Tukey's test) according to the scale of the variable (continuous or categorical). All statistical analyses were performed using SAS system for Windows, version 9.1.3 and the Enterprise Guide, version 4.1 (SAS Institute, Inc., Cary, N.C.). Statistical significance was set at $P<0.05$. Results are expressed as mean±standard deviation (SD).

Results

GSTP1 Ameliorates the Myocardial Overexpression of Inflammatory Cytokines Following Acute MI Immunoprecipitation and Western blot analyses revealed that in the acute myocardial infarction model, GSTP1 treatment did not change the formation of GSTP1-TRAF2 complexes (FIG. 9A). Western blotting revealed that although GSTP1 could reduce the cardiac tissue protein levels of activated JNK1 ($p<0.01$; FIG. 9B), there were no difference in the protein expression levels of activated P38 and NF-kB as compared to controls. Moreover, GSTP1 inhibited the cardiac tissue expressions of inflammatory cytokines including TGF-β, IL-1β, IL-2 and IL-17 ($p<0.01$; FIG. 9C) as compared to controls; although IL-10 expression levels did not significantly change following GSTP1 treatment (FIG. 9C).

GSTP1 Ameliorates the Myocardial Expression of Pro-Inflammatory Cytokines Through TRAF2-Regulated NF-kB Signaling in the Failing Myocardium Immunoprecipitation and Western blot analyses revealed that GSTP1-treated rats had significantly increased formation of GSTP1-TRAF2, GSTP1-JNK1 and GSTP1-p38 complexes in their failing cardiac tissue at 3 weeks post-MI as compared to controls ($p<0.001$; FIG. 10A). In addition, GSTP1-treated rats had significantly reduced protein expression of activated JNK1 and p38 in their failing myocardial tissue as compared to controls ($p<0.001$; FIG. 10B). Moreover, GSTP1-treated rats had lower cardiac tissue mRNA expressions of TGF-β, IL-1β, IL-2 and IL-17 as compared to controls ($P\leq0.001$; FIG. 10C). In contrast, cardiac tissue mRNA expression of the anti-inflammatory cytokine IL-10 was significantly increased in GSTP1-treated animals as compared to controls ($p<0.001$; FIG. 10C). These results show that GSTP1 treatment inhibits TRAF2-mediated JNK1, p38 and NF-kB pro-inflammatory signaling and ameliorates myocardial cytokine expression in ischemia-induced heart failure.

GSTP1 Ameliorates Remodeling in Rat Failing Myocardium

The morphometric analyses revealed that LV wall thickness was increased significantly in GSTP1-treated (2.2±0.4 mm) as compared to control rats (1.3±0.5 mm; FIGS. 11A and 11B). To analyze the effect of GSTP1 treatment on rescuing myocardial tissue in the infarct and peri-infarct areas, TUNEL assay was performed. The results of these assays show significant reduction of apoptotic events in the infarct and peri-infarct area of GSTP1-treated as compared to control animals (FIGS. 11C and 11D). These data show that GSTP1 treatment significantly reduces myocardial remodeling and post-MI myocardial tissue apoptosis in the rat failing heart.

GSTP1 Improves Cardiac Function

Having shown that GSTP1 is effective in counteracting inflammation and myocardial remodeling in a rat model of ischemia-induced heart failure and acute myocardial infarction, the LV function in the failing rat myocardium was proven. The results showed that left ventricular ejection fraction (LVEF) at 3 weeks post-MI was significantly higher in GSTP1 treated rats as compared to untreated group ($p<0.05$, FIG. 12A). Moreover, LV end-diastolic volume (LVEDV) was improved (decreased) significantly in the GSTP1 treated group at 3 weeks post-MI compared to control animals ($p<0.05$, FIG. 12B). These data show that GSTP1 treatment significantly improves LVEF and attenuates LV dilation associated with ischemia-induced heart failure.

The role of the inflammatory mediators in the pathophysiology of heart failure has gained a growing interest over the last two decades. Different experimental studies have described the negative inotropic effect of TNF-α on the LV function. Moreover, it has been reported that TNF-α promotes LV remodeling, cardiac hypertrophy and progressive cardiomyocytes loss through apoptosis. The growing evidence on the pathological role of inflammatory mediators in the setting of heart failure have resulted in a series of multicenter clinical trials that intended to target TNF-α in heart failure patients. However, the results of these trials were discouraging. One explanation of these results is that the low physiological levels of TNF-α might be important for cardiac tissue remodeling and repair. In concert with this argument, experimental studies have described an opposing role of TNF-α in cardiac tissue remodeling through its two different receptors TNFR1 and TNFR2. It has been shown that while TNFR1 aggravates remodeling, hypertrophy and apoptosis, TNFR2 ameliorates these events. However, the mechanism of TNFR2-mediated effect in heart failure remains unclear. Recently, it has been shown that TRAF2 is a central regulator of TNF-α signaling that mediates MAPK activation. Moreover, the interaction between TNFR2 and TRAF2 results in activation of NFκB. Furthermore, it has been reported that GSTP1 is an important negative regulator of TNF-α-induced signaling by forming interactions with TRAF2. In line with this, GSTP1 could inhibit MAPK activation in malignant cell lines indirectly through its interaction with TRAF2 or directly through its interaction with JNK1 and P38. These results together with the findings of the present invention that GSTP1 and TRAF2 are upregulated in patients with heart failure show that GSTP1-TRAF2 complex formation is associated with the pathogenesis of heart failure. Tissue culture experiments in heart failure patients revealed that although the addition of TNF-α could suppress the anti-inflammatory effect of GSTP1, this effect can be retained by increasing the GSTP1 dose. The anti-inflammatory properties of GSTP1 were approved by the current results in vivo. The experimental model used herein revealed that GSTP1 was able to ameliorate the inflammatory reaction and decrease the cardiac remodeling after the induction of MI. Interestingly, GSTP1 was not only able to suppress the proinflammatory mediators like; IL-1, IL-2, JNK1, P38 and NF-kB but also could increase the expression of the anti-inflammatory cytokine IL-10. Moreover, the results according to the present invention revealed that GSTP1 protects the cardiac tissue against apoptosis in the failing heart. In concert with this, it has been shown in oncological settings that GSTP1 attenuates the auto-phosphorylation of TRAF2-enhanced apoptosis signal-regulating kinase1 (ASK1) and thus inhibits TRAF2-ASK1-induced cell apoptosis by suppressing the interaction of TRAF2 and ASK1.

In conclusion, the present invention provides a novel function of GSTP1 in modulating TNF-α/TRAF2 elicited JNK1/p38 activation in heart failure. The selective inhibition of TNF-α/TRAF2-mediated inflammatory signaling by GSTP1 was due to the present animal model shown to be a beneficial treatment for patients with cardiomyopathies or ischemic heart diseases, especially for patients with myocardial infarction and heart failure.

The invention claimed is:

1. A method for treating cardiomyopathy (CMP) or ischemic heart disease (IHD) comprising:
    administering to a human individual in need thereof glutathione S-transferase P1 (GSTP1) in an amount effective to treat CMP or, IHD, wherein the human individual in need thereof is a patient having been diagnosed with CMP and/or IHD.

2. The method according to claim 1, wherein the cardiomyopathy is dilated cardiomyopathy; obstructive hypertrophic cardiomyopathy; other hypertrophic cardiomyopathy; ischemic cardiomyopathy, endomyocardial (eosinophilic) disease; endocardial fibroelastosis; other restrictive cardiomyopathy; alcoholic cardiomyopathy, cardiomyopathy due to drugs and other external agents, unspecified cardiomyopathies; cardiomyopathy in infectious and parasitic diseases; cardiomyopathy in metabolic diseases; cardiomyopathy in nutritional diseases; Gouty tophi of heart or thyrotoxic heart disease.

3. The method for treating ischemic heart disease comprising:
    administering to a human individual in need thereof glutathione S-transferase P1 (GSTP1) in an amount effective to treat cardiomyopathies or ischemic heart diseases, wherein the ischemic heart disease is caused by myocardial infarction, by hypertension, or by myocarditis.

4. The method according to claim 3, wherein the myocarditis is acute myocarditis; isolated myocarditis, myocarditis in a bacterial disease; myocarditis in a viral disease; acute or chronic myocarditis in Chagas' disease, myocarditis in toxoplasmosis, rheumatoid myocarditis or sarcoid myocarditis.

5. The method according to claim 1, wherein the GSTP1 is parentally administered.

6. The method according to claim 1, wherein the GSTP1 is administered in a dosage of 0.001 to 100 mg GSTP1/kg to a human individual.

7. The method according to claim 1, wherein the GSTP1 is administered in a dosage of 0.1 to 10000 U GSTP1/kg to a human individual.

8. The method according to claim 2, wherein the dilated cardiomyopathy is congestive cardiomyopathy; the obstructive hypertrophic cardiomyopathy is hypertrophic subaortic stenosis; the other hypertrophic cardiomyopathy is nonobstructive hypertrophic cardiomyopathy; the endomyocardial (eosinophilic) disease is endomyocardial (tropical) fibrosis or Loffler's endocarditis; the endocardial fibroelastosis is congenital cardiomyopathy; the other restrictive cardiomyopathy is constrictive cardiomyopathy NOS; the unspecified cardiomyopathies is cardiomyopathy (primary) (secondary) NOS; the cardiomyopathy in infectious and parasitic diseases is cardiomyopathy in diphtheria; the cardiomyopathy in metabolic diseases is cardiac amyloidosis; and the cardiomyopathy in nutritional diseases is nutritional cardiomyopathy NOS.

9. The method according to claim 4, wherein the acute myocarditis is infective myocarditis; the myocarditis in a bacterial disease is diphtheritic, gonococcal, meningococcal, syphilitic or tuberculous myocarditis; and the myocarditis in a viral disease is influenzal myocarditis or mumps myocarditis.

10. The method according to claim 9, wherein the infective myocarditis is septic myocarditis.

11. The method according to claim 5, wherein the GSTP1 is administered intraperitoneally or intravenously.

12. The method according to claim 6, wherein the GSTP1 is administered in a dosage of 0.01 to 10 mg GSTP1/kg.

13. The method according to claim 12, wherein the GSTP1 is administered in a dosage of 0.1 to 1 mg GSTP1/kg via intravenous administration.

14. The method according to claim 7, wherein the GSTP1 is administered in a dosage of 1 to 1000 U GSTP1/kg.

15. The method according to claim 14, wherein the GSTP1 is administered in a dosage of 10 to 100 U GSTP1/kg via intravenous administration.

16. The method of claim 1, wherein the human individual is a human CMP or IHD patient, a patient with hypertension or an angina pectoris patient.

* * * * *

SEQUENCE LISTING

```
<160> NUMBER OF SEQ ID NOS: 10

<210> SEQ ID NO 1
<211> LENGTH: 210
<212> TYPE: PRT
<213> ORGANISM: Homo sapiens

<400> SEQUENCE: 1

Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
        115                 120                 125

Pro Phe Glu Thr Leu Leu Ser Gln Asn Gln Gly Gly Lys Thr Phe Ile
    130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190

Phe Leu Ala Ser Pro Glu Tyr Val Asn Leu Pro Ile Asn Gly Asn Gly
        195                 200                 205

Lys Gln
    210

<210> SEQ ID NO 2
<211> LENGTH: 633
<212> TYPE: DNA
<213> ORGANISM: Homo sapiens

<400> SEQUENCE: 2
atgccgccct acaccgtggt ctatttccca gttcgaggcc gctgcgcggc cctgcgcatg      60
ctgctggcag atcagggcca gagctggaag gaggaggtgg tgaccgtgga gacgtggcag     120
gagggctcac tcaaagcctc ctgcctatac gggcagctcc ccaagttcca ggacggagac     180
ctcaccctgt accagtccaa taccatcctg cgtcacctgg gccgcaccct tgggctctat     240
```

```
gggaaggacc agcaggaggc agccctggtg gacatggtga atgacggcgt ggaggacctc      300
cgctgcaaat acgtctccct catctacacc aactatgagg cgggcaagga tgactatgtg      360
aaggcactgc ccgggcaact gaagcctttt gagaccctgc tgtcccagaa ccagggaggc      420
aagaccttca ttgtgggaga ccagatctcc ttcgctgact acaacctgct ggacttgctg      480
ctgatccatg aggtcctagc ccctggctgc ctggatgcgt tcccctgct ctcagcatat       540 gtggggcgcc tcagcgcccg gcccaagctc aaggccttcc tggcctcccc tgagtacgtg      600
aacctcccca tcaatggcaa cgggaaacag tga                                   633

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ggcaactgaa gccttttgag                                                   20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tcatggatca gcagcaagtc                                                   20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gcagaaggtc ttggagatgg                                                   20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ggtggagcag cattaaggtc                                                   20

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gatgagtatg cctgccgtgt g                                                 21

<210> SEQ ID NO 8
<211> LENGTH: 19
<212> TYPE: DNA
<213> ORGANISM: Artificial Sequence
```

```
<220> FEATURE:
<223> OTHER INFORMATION: Primer

<400> SEQUENCE: 8
caatccaaat gcggcatct                                                    19

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccaaaggtgg tgagcttcat                                                   20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tctacccagc atggaggaac                                                   20
```